US012465771B2

(12) United States Patent
Ward

(10) Patent No.: US 12,465,771 B2
(45) Date of Patent: Nov. 11, 2025

(54) DELIVERY DEVICE AND METHOD FOR PERCUTANEOUSLY IMPLANTING A MEDICAL IMPLANT

(71) Applicant: Capri Medical Limited, Dublin (IE)

(72) Inventor: Fergal Ward, Dublin (IE)

(73) Assignee: Capri Medical Limited, Dublin (IE)

( * ) Notice: Subject to any disclaimer, the term of this patent is extended or adjusted under 35 U.S.C. 154(b) by 666 days.

(21) Appl. No.: 17/841,062

(22) Filed: Jun. 15, 2022

(65) Prior Publication Data

US 2023/0405310 A1 Dec. 21, 2023

(51) Int. Cl.

*A61N 1/372* (2006.01)
*A61N 1/05* (2006.01)
*A61N 1/378* (2006.01)
*A61N 1/36* (2006.01)

(52) U.S. Cl.

CPC ....... *A61N 1/37205* (2013.01); *A61N 1/0551* (2013.01); *A61N 1/3787* (2013.01); *A61N 1/36071* (2013.01)

(58) Field of Classification Search

None
See application file for complete search history.

(56) References Cited

U.S. PATENT DOCUMENTS 8,606,355 B1* 12/2013 Krause ............... A61N 1/36114 607/9
2008/0269716 A1 10/2008 Bonde et al.
2011/0160801 A1* 6/2011 Markowitz ........ A61N 1/37217 607/60
2013/0125395 A1* 5/2013 Pianca ..................... A61N 1/05 29/874
2016/0059003 A1* 3/2016 Eggen .................. A61N 1/3756 606/129
2020/0000367 A1* 1/2020 Oren ...................... A61B 5/068
2020/0101279 A1* 4/2020 Drake ................ A61N 1/37518
2020/0230369 A1* 7/2020 Ma .................... A61M 25/0693
2021/0169368 A1* 6/2021 Govari ................... A61B 5/053
2023/0190364 A1* 6/2023 Curran ................... A61B 18/00 606/41

FOREIGN PATENT DOCUMENTS

EP 3616748 A1 3/2020
WO 2020069293 A1 4/2020

* cited by examiner

*Primary Examiner* — Kennedy Schaetzle
(74) *Attorney, Agent, or Firm* — ArentFox Schiff LLP; Bruce D. Jobse

(57) ABSTRACT

A delivery device (10) for percutaneously implanting a medical implant (1) in tissue of a patient includes a delivery sheath (12, 13, 53, 61, 62, 65, 66) adapted to at least partially surround the medical implant and carry the medical implant for percutaneous delivery in the patient's tissue. The delivery device also includes a power delivery system (37) adapted to provide electric power to the medical implant within the delivery sheath.

20 Claims, 20 Drawing Sheets

DELIVERY DEVICE AND METHOD FOR PERCUTANEOUSLY IMPLANTING A MEDICAL IMPLANT

FIELD OF THE INVENTION

This invention relates to a delivery device and method for percutaneously implanting a medical implant, such as a neuromodulation implant, into a patient's tissue, a medical implant, and a method of percutaneously implanting a medical implant.

BACKGROUND

It is known to provide an implantable neurostimulator comprising a housing and an electrode. A power antenna, microcontroller, and communication antenna are disposed in the housing for receiving power from an external source and receiving/transmitting sensor information relating to the electrode. A delivery system can be used to position the neurostimulator in a patient, in particular proximate to a nerve, by cutting an opening in the patient and passing the delivery system into the opening to position the implantable neurostimulator.

BRIEF SUMMARY OF THE DISCLOSURE

In accordance with a first aspect of the present disclosure there is provided a delivery device for percutaneously implanting a medical implant in tissue of a patient, the delivery device comprising:

- a delivery sheath adapted to at least partially surround the medical implant and carry the medical implant for percutaneous delivery in the patient's tissue, and
- a power delivery system adapted to provide electric power to the medical implant within the delivery sheath.

The power delivery system advantageously permits the medical implant to be powered during implantation to test the position of the medical implant prior to it being fully deployed.

In examples, the medical implant may comprise power terminals. In such examples the power delivery system may comprise electrical contacts disposed in the delivery sheath for forming an electrical connection with the power terminals of the medical implant.

In examples, the medical implant may comprise a wireless power receiver. In such examples the power delivery system may comprise a wireless power transmitter arranged to transmit wireless power to the wireless power receiver of the medical implant. The wireless power transmitter may be disposed in the delivery sheath.

In examples, the delivery device may further comprise a power source, for example a battery. In other examples the delivery device may further comprise a connector for an external power source, such as mains power or an external battery.

In examples, the delivery device may comprise a handle and the delivery sheath extends from the handle. In some examples at least a part of the delivery sheath may be retractable relative to the handle to partially expose the medical implant during percutaneous delivery in the patient's tissue. In examples, at least a part of the delivery sheath may be retractable to release the medical implant in the patient's tissue. In examples, the delivery sheath may comprise a needle, or a cannula.

In examples, the medical implant may comprise a housing portion and an elongate electrode lead extending from the housing portion. The delivery sheath may be adapted to carry the housing portion for percutaneous delivery in the patient's tissue. In examples, the delivery sheath may also be adapted to carry the elongate electrode lead for percutaneous delivery in the patient's tissue. In examples, the delivery sheath may comprise a retractable portion adapted to carry the elongate electrode lead for percutaneous delivery in the patient's tissue.

In examples, the medical implant is a neurostimulator implant. In such examples the delivery device may further comprise a sensor operable to detect a reaction of the patient when the power delivery system provides electric power to the neurostimulator implant during percutaneous delivery. In particular, the medical implant may comprise one or more electrodes operable to stimulate a nerve of the patient, and the sensor may detect a reaction of the patient to such stimulation. In examples, the sensor may be configured to detect a movement reaction of the patient. In examples, the sensor is configured to detect neural signals.

In examples, the delivery device may further comprise a graphical user interface (GUI) operable to display information received from the sensor. The GUI may also display operating characteristics of the medical (neurostimulator) implant, such as an operating frequency or amplitude. The GUI may also provide a user input for controlling the delivery device, for example the power delivery system.

In accordance with a second aspect of present disclosure there is also provided a medical implant for implantation in tissue of a patient, the neurostimulator implant comprising:

- a wireless power receiver, and
- power terminals for forming an electrical connection with electrical connectors of a delivery device during implantation of the medical implant.

Advantageously, the power terminals allow the medical implant to be powered in a delivery device, during implantation, so the implantation site of the medical implant can be tested before the medical implant is fully deployed. Such direct powering via the power terminals may be more reliable and efficient that powering using the wireless power receiver while the medical implant is held in the delivery device.

In examples, the medical implant may further comprise a housing portion, and the power terminals may be disposed on the housing portion. The housing portion may additionally house electronics components of the medical implant, including the wireless power receiver.

In examples, the medical implant may further comprise an elongate electrode lead extending from the housing portion, and the elongate electrode lead may comprise an electrode. The electrode may be a stimulating electrode and/or a sensing electrode.

In accordance with a third aspect of the present disclosure there is also provided a medical implant for implantation in tissue of a patient, the medical implant comprising:

- a first wireless power receiver for wireless power coupling with an external wireless power transmitter when implanted in the patient, and
- a second wireless power receiver for wireless power coupling with a wireless power transmitter of a delivery device during implantation of the medical implant.

In examples, the medical implant may be a neurostimulator implant operate to stimulate a nerve of the patient. In other examples, the medical implant may be a diagnostic implant, particularly a diagnostic implant operable to detect neural signals. In other examples, the diagnostic implant may detect one or more patient vital signs, for example body temperature, heart rate, electromyography (EMG), electrocardiogram (ECG), respiration rate, blood pressure, and/or blood gas concentration (e.g., oxygen, carbon dioxide, carbon monoxide).

In accordance with a fourth aspect of the present disclosure there is also provided a method of percutaneously implanting a medical implant in tissue of a patient, the method comprising:

providing a delivery device having a power delivery system and a delivery sheath carrying the medical implant, percutaneously positioning the delivery sheath in the patient's tissue, and testing the position of the medical implant by powering the medical implant within the delivery sheath by the power delivery system of the delivery device.

Advantageously, the medical implant can thereby be powered during implantation to test the position of the medical implant prior to it being fully deployed.

In examples, the method may further comprise exposing an electrode of the medical implant while testing the position of the medical implant.

In examples, the method may further comprise repositioning the delivery sheath based on feedback from testing the position of the medical implant. Feedback may be provided by the patient (e.g., pain or tingling sensations), or by visual feedback from the operator (e.g., a movement or other change), or by a sensor.

In examples, the medical implant may comprise a neurostimulator implant. In such examples, the method may further comprise detecting a reaction of the patient while testing the position of the neurostimulator implant. In examples, detecting a reaction of the patient may comprise detecting a movement reaction of the patient. In examples, detecting a reaction of the patient may comprise detecting a neural signal of the patient.

In examples, the method may further comprise displaying information received from the sensor on a graphical user interface. In examples, the method may further comprise displaying information about operation of the medical implant on a graphical user interface. For example, the method may comprise displaying operating characteristics of the medical implant.

In accordance with a fifth present disclosure there is also provided a delivery device for percutaneously implanting a medical implant in tissue of a patient, the delivery device comprising:

a delivery sheath adapted to at least partially surround the medical implant and carry the medical implant for percutaneous delivery in the patient's tissue, and an impedance sensor comprising a first electrode on the delivery sheath and a second electrode arranged to contact the patient at a location spaced from the first electrode, wherein the impedance sensor is operable to detect an electrical impedance between the first electrode and the second electrode to detect a change in the tissue at the delivery sheath during percutaneous delivery of the medical implant.

Advantageously, the detected electrical impedance may inform the operator when the delivery sheath is close to, or passing into, a different tissue type. This can assist with positioning the delivery sheath and the medical implant during implantation.

In examples, the first electrode may be disposed at or near a tip of the delivery sheath. In examples, the second electrode may be positionable against the skin of the patient proximate to the percutaneous delivery site (e.g., adhered or strapped to the skin).

In examples, the delivery device may further comprise an impedance analyser configured to analyse the detected electrical impedance. In examples, the impedance analyser is configured to compare the detected electrical impedance to a threshold value. In examples, the impedance analyser may be configured to compare the detected electrical impedance to a database or other comparable data, for example to determine a tissue type or anatomical feature. In examples, the database or comparable data may be provided in a distributed location and the impedance analyser may communicate via a wireless communications channel.

In examples, the delivery device may further comprise a graphical user interface (GUI) to display information received from the impedance analyser. The GUI may also display operating characteristics of the medical implant, such as an operating frequency or amplitude. The GUI may also provide a user input for controlling the delivery device, for example the impedance sensor system.

In examples, the delivery device may further comprise a power delivery system adapted to provide electrical power to the medical implant within the delivery sheath. The power delivery system may comprise any of the features described above in relation to the first to fourth aspects of the present disclosure.

In accordance with a sixth aspect of the present disclosure there is also provided a method of percutaneously implanting a medical implant in tissue of a patient, the method comprising:

percutaneously positioning a delivery sheath of a delivery device, the delivery sheath carrying the medical implant, detecting an electrical impedance between a first electrode on the delivery sheath and a second electrode in contact with the patient at a location spaced from the first electrode, and analysing the detected electrical impedance to detect a change in the tissue at the delivery sheath during percutaneous delivery of the medical implant.

Advantageously, the detected electrical impedance may inform the operator when the delivery sheath is close to, or passing into, a different tissue type. This can assist with positioning the delivery sheath and the medical implant during implantation.

In examples, the method may further comprise comparing the detected electrical impedance to a threshold value. In examples, the method may comprise comparing the detected electrical impedance to a database or other comparable data, for example to determine a tissue type or anatomical feature. In examples, the database or comparable data may be provided in a distributed location and the impedance analyser may communicate via a wireless communications channel.

In examples, the method may further comprise displaying, on a graphical user interface, information relating to the detected electrical impedance.

In examples, the method may further comprise powering the medical implant within the delivery sheath to test a position of the medical implant before fully releasing the medical implant from the delivery sheath. The method may further comprise any of the features described above in relation to the first to fourth aspects of the present disclosure.

In accordance with a seventh aspect of the present disclosure there is also provided a method of percutaneously delivering a neurostimulator implant into tissue of a patient, the method comprising:

percutaneously positioning a delivery sheath carrying the neurostimulator implant;

detecting a change in electrical impedance between a first electrode on the delivery sheath and a second electrode in contact with the patient at a location spaced from the first electrode, the change in electrical impedance being indicative of a change in the patient's tissue at the delivery sheath; and powering the neurostimulator implant within the delivery sheath to test a position of the neurostimulator implant relative to a nerve of the patient.

In examples, the method may further positioning the delivery sheath in proximity to the nerve based on the detected electrical impedance, and subsequently testing the position of the neurostimulator implant relative to the nerve by powering the neurostimulator implant within the delivery sheath.

Advantageously, the detected change in electrical impedance may inform the operator that the delivery sheath is close to the nerve or other target anatomical site, while powering the neurostimulator implant within the delivery device allows the operator to test the implantation site before fully deploying the neurostimulator implant. Accordingly, the implantation position can be improved and any difficult or damaging removal or repositioning of the neurostimulator implant may be avoided.

In examples, the method may further comprise partially retracting the delivery sheath to expose an electrode of the neurostimulator implant before powering the neurostimulator implant within the delivery sheath.

According to a further aspect of the present invention there is also provided a delivery device for percutaneously implanting a medical implant in tissue of a patient, the delivery device comprising a delivery sheath adapted to be percutaneously positioned and having a lumen adapted to carry medical implant for percutaneous implantation.

In examples, the delivery sheath comprises a cannula or needle for percutaneous implantation of the medical implant. The cannula or needle can be percutaneously positioned and the medical implant can be ejected from the cannula or needle, for example by a pusher. The needle may comprise a sharp tip, for example a bevel tip. The needle or cannula may be adapted to puncture the patient's skin, and/or may be inserted through an incision in the patient's skin.

In examples, the delivery sheath may comprise a first portion that holds a first part of the medical implant (e.g., a housing portion), and a second portion protruding from the first portion for holding second part of the medical implant (e.g., an electrode lead). The first and second portions may be fixed to one another and have different diameters (e.g., the second portion may have a smaller diameter than the first portion). The second portion may include a slot extending along its length, from the first portion to its tip. The first portion may also have a slot or opening in the side, aligned with the slot of the second portion. In this way, the medical implant can be deployed by a pusher pushing the medical implant out of the first and second portions. For example the housing portion may be pushed out of the first portion via the slot or opening, and the delivery device can then be retracted to fully implant the medical implant.

In examples, the medical implant may comprise a housing portion (e.g., housing electronics of the medical implant, such as a wireless power receiver), and an elongate electrode lead extending from the housing portion. In examples, the delivery sheath may comprise a first needle or cannula adapted to hold the medical implant such that the electrode lead is directed away from a tip of the needle. A second needle may hold the electrode lead within the first needle or cannula and may be extendible beyond the tip of the first needle or cannula to implant the electrode lead.

In examples, the delivery device may further comprise a power delivery system for powering the medical implant within the delivery device.

In examples, the delivery device may further comprise an impedance sensor system to detect a change in the tissue at the delivery sheath during percutaneous delivery of the medical implant.

In examples, the delivery device may further comprise other features of the delivery device described above with reference to the first to seventh aspects of the present disclosure.

According to a further aspect of the present invention there is also provided a medical implant comprising a wireless power receiver adapted to wirelessly couple with an external device to receive wireless power, and a wireless power transmitter adapted to wireless couple with a further medical implant to transmit wireless power to the further medical implant.

The medical implant may comprise a first portion holding the wireless power receiver and a second portion holding the wireless power transmitter. The second portion may be implantable at a greater depth (relative to the skin) than the first portion. The medical implant may thereby act as a power relay for improving wireless power transmission to the further medical implant. In examples, the further medical implant may be a deep tissue medical implant, such as a neurostimulator implant, or a diagnostic implant, or a pacemaker implant, or the like.

BRIEF DESCRIPTION OF THE DRAWINGS

Embodiments of the invention are further described hereinafter with reference to the accompanying drawings, in which.

DETAILED DESCRIPTION

Figure 1:
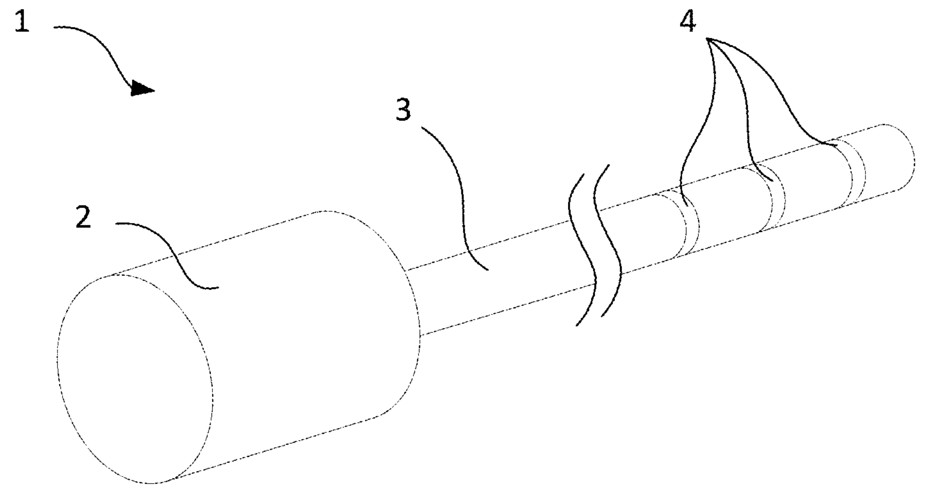
FIG. 1 shows an example medical implant.

FIG. 1 schematically illustrates a medical implant 1. In examples, the medical implant 1 may be a neurostimulator implant or a diagnostic implant. The medical implant 1 comprises a housing portion 2 and an elongate electrode lead 3. The housing portion 2 may house electronics components of the medical implant 1, including for example a printed circuit board, a wireless communications receiver/transmitter, a wireless power receiver, and/or sensor electronics, as described further hereinafter. In examples, the housing portion is hermetically sealed. The housing portion 2 may comprise a cylindrical casing with sealed ends, or may comprise a wrapping or other envelopment of the components within the housing portion 2.

In examples, the electrode lead 3 extends from the housing portion 2 and is flexible. The electrode lead 3 includes at least one electrode 4, in some examples multiple electrodes 4 spaced along the length of the electrode lead 3. The electrodes 4 are connected to the electronics within the housing portion 2.

In examples, the housing portion 2 may have a diameter of between about 0.5 millimetres and about 5 millimetres, for example between about 1 millimetre and about 3 millimetres. The housing portion 2 may have a length of up to about 10 millimetres, for example up to about 5 millimetres. In examples, the electrode lead 3 may have a diameter of between about 0.3 millimetres to about 1.5 millimetres, for example between about 0.5 millimetres and 1.3 millimetres. The electrode lead 3 may have a length of up to about 100 millimetres, for example up to about 50 millimetres, for example about 50 millimetres. However, it will be appreciated that the dimensions of the housing portion 2 would correspond to the size of the electronics housed within the housing portion 2, and the length of the electrode lead 3 would correspond to the anatomy surrounding the targeted nerve, so a shorter or longer electrode lead 3 may be appropriate depending on the depth of the nerve within the muscle tissue As described further hereinafter, the medical implant 1 is implantable in a patient and operable to sense and/or stimulate a nerve. In some examples, the medical implant 1 is implantable to sense and/or stimulate the greater occipital nerve, although the same or similar implant may be implantable to sense and/or stimulate other nerves, particularly other peripheral nerves of the peripheral nervous system. In examples, the medical implant 1 may be implantable to sense and/or stimulate the tibial nerve, the sacral nerve (e.g., to treat urinary incontinence) or the vagus nerve (e.g., to regulate pancreatic secretion).

Figure 2:
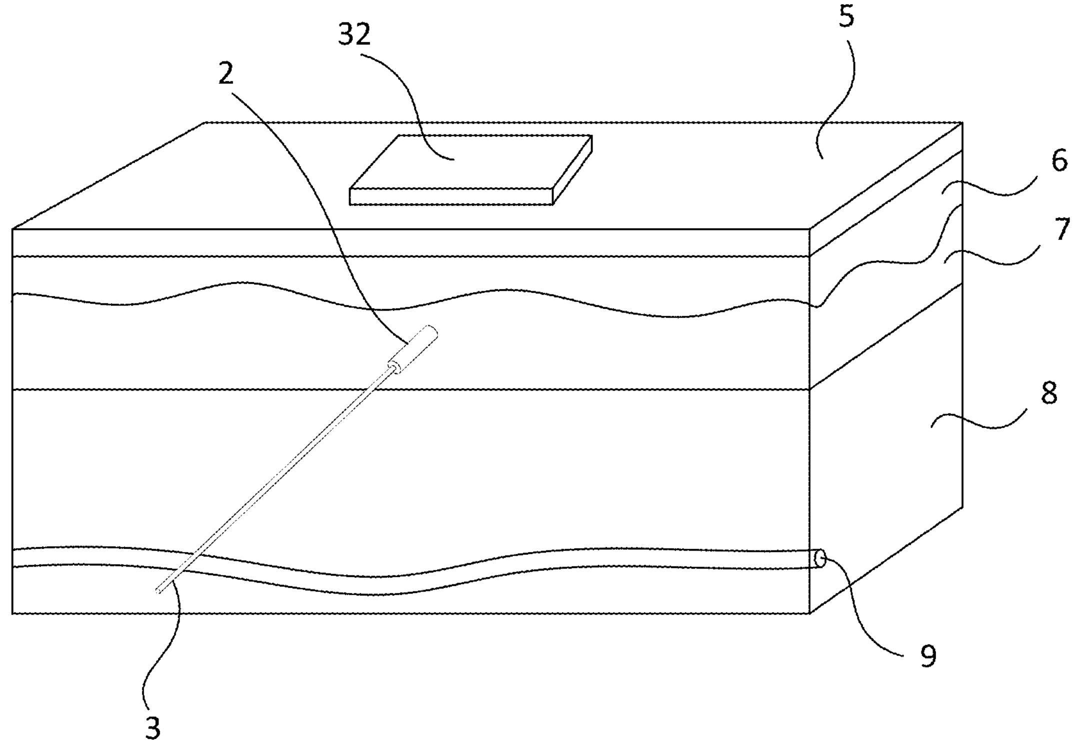
FIG. 2 show the medical implant in position in a patient, particularly in a subcutaneous position.

FIG. 2 shows the medical implant 1 once implanted in a patient. The medical implant 1 is positioned below the surface of the skin, in particular below the epidermis 5. The housing portion 2 may be positioned in the dermis 6 or in the subcutaneous tissue 7. Positioning the housing portion 2 in the subcutaneous tissue 7 may be beneficial to cause less damage and/or irritation to the patient.

As illustrated, the electrode lead 3 extends from the housing portion 2, through the underlying tissue, in particular muscle 8, to a position proximal to the target nerve 9. The electrode lead 3 is positioned such that the electrodes (4, see FIG. 1) are in contact with or proximal to the nerve 9, and so the electrodes 4 can be used to sense and/or stimulate the nerve 9.

The medical implant 1 may also include one or more anti-migration members. The anti-migration members may be provided on the housing portion 2 and/or on the electrode lead 3 and function to hold the medical implant 1 in position in the patient's tissue.

In examples, the medical implant 2 is battery-less, and does not have an integrated power source. An external device 32 can wirelessly power the medical implant 1. The external device 32 may additionally wirelessly communicate with the medical implant 1, in particular the electronics in the housing portion 2. The medical implant 1 may contain a wireless communications receiver/transmitter for communicating with the external device 32. The medical implant 1 may also have a processor or controller configured to operate the medical implant 1. The external device 32 may be positioned on the skin proximal to the medical implant 1. The external device 32 may be adhered to the skin proximal to the medical implant 1. The external device 32 may be a wearable device.

In examples, the medical implant 1 is a neurostimulator implant. The medical implant 1 may be implanted to target a particular nerve or nerve grouping, such as the greater occipital nerve.

In operation, the electrodes 4 of a neurostimulator implant are provided with an electrical signal, such as a current, to stimulate the nerve. In examples, the electrical signal may be a voltage-regulated stimulation. Such stimulation can provide relief for chronic pain, for example occipital neuralgia, intractable migraine, and/or other therapeutic benefits.

In other examples, the medical implant 1 may be a diagnostic implant, for example a neurodiagnostic implant, operable to detect one or more neural signals in a nerve. In such examples the electrodes 4 are operable to detect neural signals. The neural signals may be analysed for the purposes of detecting, monitoring and/or diagnosing a condition.

In other examples, the medical implant 1 may be a diagnostic implant operable to detect one or more patient vital signs, for example body temperature, heart rate, electromyography (EMG), electrocardiogram (ECG), respiration rate, blood pressure, and/or blood gas concentration (e.g., oxygen, carbon dioxide, carbon monoxide).

Figure 3A:
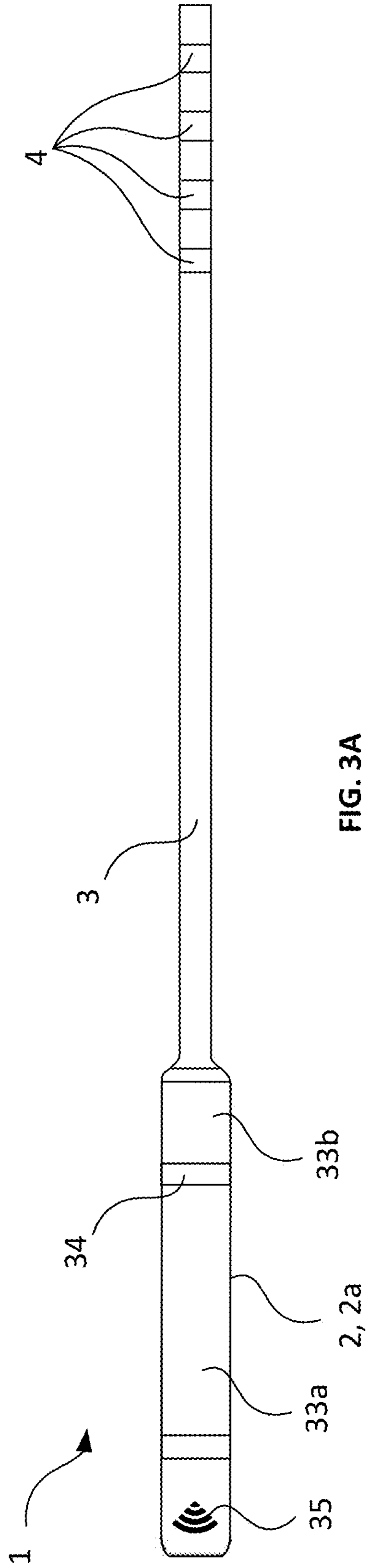
FIGS. 3A to 3D illustrate alternative example medical implants.
Figure 3B:
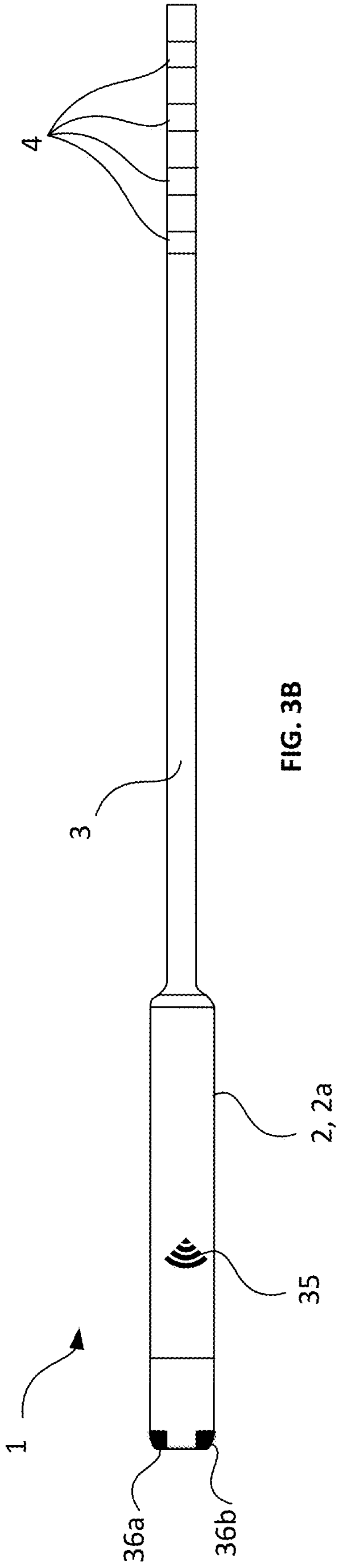
Figure 3C:
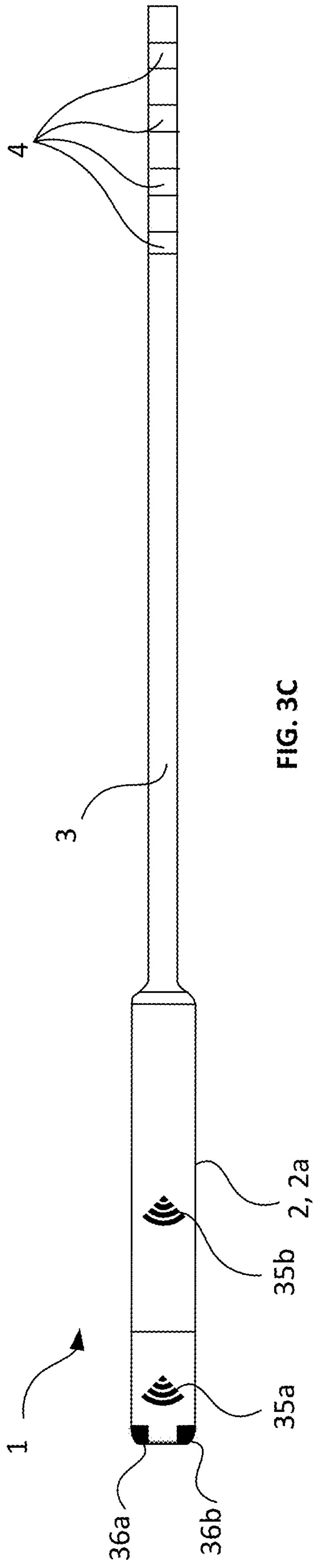
Figure 3D:
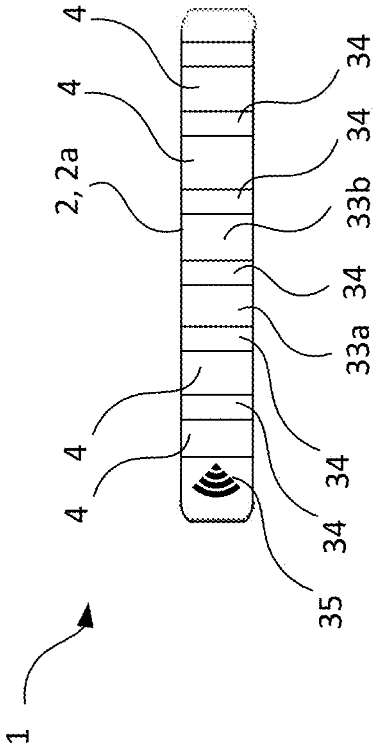

FIGS. 3A to 3D illustrate alternative examples of the medical implant 1. In each example, the medical implant 1 has a housing portion 2 and one or more electrodes 4. In the examples of FIGS. 3A to 3C the medical implant 1 includes an electrode lead 3 and electrodes 4 formed on the electrode lead 3. In the example of FIG. 3D the medical implant 1 does not comprise an electrode lead 3, and the electrodes 4 are formed on the housing portion 2. The example of FIG. 3D may be a neurostimulator implant or diagnostic implant implantable proximate to a nerve in the same manner as described above.

In the examples of FIGS. 3A to 3D the housing portion 2 comprises a casing 2*a*. The casing 2*a* may be cylindrical and house electronic components within. The housing portion 2 comprises a wireless power receiver 35, 35*b* for receiving wireless power from an external device (32, see FIG. 2) once implanted in the patient. In the examples of FIGS. 3A to 3C the medical implant 1 also comprises an electrode lead 3 extending from the housing portion 2, and the electrodes 4 may be provided on the electrode lead 3.

As shown in FIG. 3A, the housing portion 2 comprises first and second power terminals 33*a*, 33*b* formed on the casing 2*a* of the housing portion 2. In particular, the first and second power terminals 33*a*, 33*b* are conductive areas of the casing 2*a* and are separated by an insulated portion 34. The first and second power terminals 33*a*, 33*b* may be point contacts. Alternatively, the first and second power terminals 33*a*, 33*b* may be conductive areas of the casing 2*a* and so extend over a portion of the length of the casing 2*a*. As described further hereinafter, the first and second power terminals 33*a*, 33*b* can be connected with a power delivery system within a delivery device to power the medical implant 1 within the delivery device during implantation. The wireless power receiver 35 is disposed in the housing portion 2 and may be spaced from the first and second power terminals 33*a*, 33*b*.

In the example of FIG. 3B, the housing portion 2 comprises first and second power terminals 36*a*, 36*b* formed at the end of the housing portion 2, in particular an end of the casing 2*a* opposite to the electrode lead 3. As described further hereinafter, the first and second power terminals 36*a*, 36*b* can be connected with a power delivery system within a delivery device to power the medical implant 1 within the delivery device during implantation. The wireless power receiver 35 is disposed in the housing portion 2 and may be spaced from the first and second power terminals 33*a*, 33*b*.

In the example of FIG. 3C, the housing portion 2 comprises a first wireless power receiver 35*a* and a second wireless power receiver 35*b*. As described further hereinafter, the first wireless power receiver 35*a* is arranged to receive wireless power while the medical implant 1 is in a delivery device, during implantation. The second wireless power receiver 35*b* is arranged to receive wireless power from an external device (32, see FIG. 2) once the medical implant 1 has been implanted in the patient. In this example, as illustrated, the housing portion 2 optionally also comprises first and second power terminals 36*a*, 36*b* like those described with reference to FIG. 3B. In another example, the housing portion 2 may comprise first and second power terminals 33*a*, 33*b* like those described with reference to FIG. 3A.

In the example of FIG. 3D, the medical implant 1 comprises a housing portion 2, and no electrode lead 3 as per the examples of FIGS. 3A to 3C. In this example, the casing 2*a* of the housing portion 2 has the first and second power terminals 33*a*, 33*b*, separated by insulated portions 34, for connecting with a power delivery system of a delivery device during implantation. The casing 2*a* also comprises the electrodes 4, separated by other insulated areas 34. In some examples, as illustrated, the housing portion 2 also holds a wireless power receiver 35. The wireless power receiver 35 is disposed in the housing portion 2 and may be spaced from the first and second power terminals 33*a*, 33*b* and from the electrodes 4.

In the examples of FIGS. 3B to 3D the medical implant 1 comprises a plurality of electrodes 4, and power terminals 33*a*, 33*b*, 36*a*, 36*b* for connecting to a power delivery system of a delivery device during implantation. It will be appreciated that after implantation the power terminals 33*a*, 33*b*, 36*a*, 36*b* may act as further electrodes 4 (i.e., they may be operated to sense neural signals and/or provide neural stimulation).

Figure 4A:
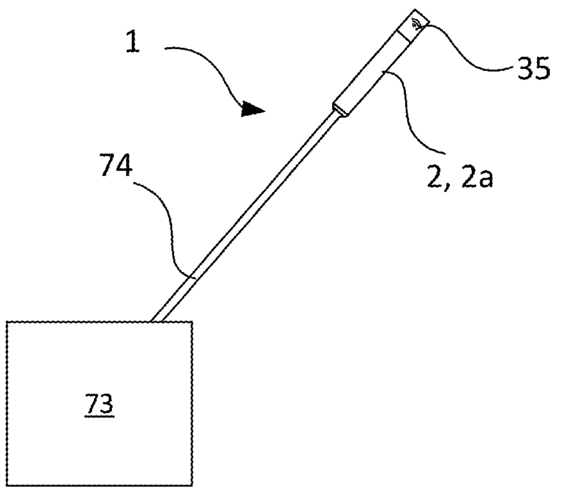
FIGS. 4A and 4B illustrate alternative medical implants used to relay wireless power to a further medical implant.
Figure 4B:
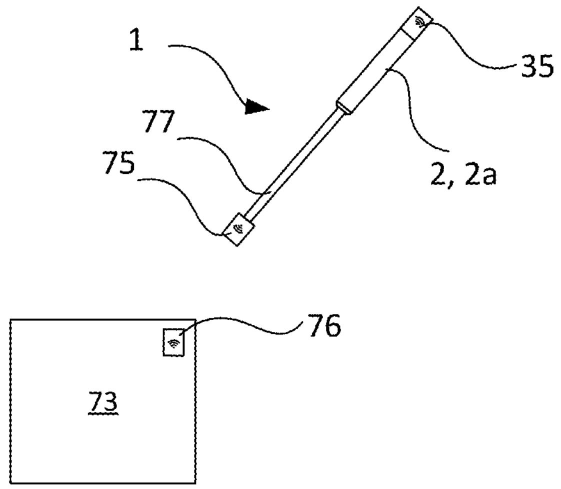

FIGS. 4A and 4B illustrate an alternative medical implant 1, for use in conjunction with a further medical implant 73. The further medical implant 73 may be a deep tissue implant, for example a pacemaker. In these examples, the medical implant 1 can act as a wireless power receiver or as a wireless power relay for the further medical implant 73. In the example of FIG. 4A the medical implant 1 may be connected to the further medical implant 73 by a wire 74. The medical implant 1 comprises a wireless power receiver 35 as described above, and transfers power to the further medical implant 73 via the wire 74. The medical implant 1 can be implanted at a lower depth in the tissue than the further medical implant 73, providing improved wireless power coupling due to the decreased distance from the external wireless power transmitter. In the example of FIG. 4B, the medical implant comprises a wireless power receiver 35 and a wireless power transmitter 75 and is arranged to relay power to a wireless power receiver 76 of the further medical implant 73. The wireless power transmitter 75 of the medical implant 1 may be connected to the housing portion 2 by a wire 77, as illustrated, or it may be within the housing portion 2 and the wire 77 may be omitted. The medical implant 1 can be implanted at a lower depth in the tissue than the further medical implant 73, providing improved wireless power coupling. In the examples of FIGS. 4A and 4B the medical implant 1 may comprise power terminals 33*a*, 33*b*, 36*a*, 36*b* and/or wireless power receiver 35*a* (and other features as described with reference to FIGS. 3A to 3D) that allow the medical implant 1 to receive power within a delivery device during implantation, as described further hereinafter.

Figure 5A:
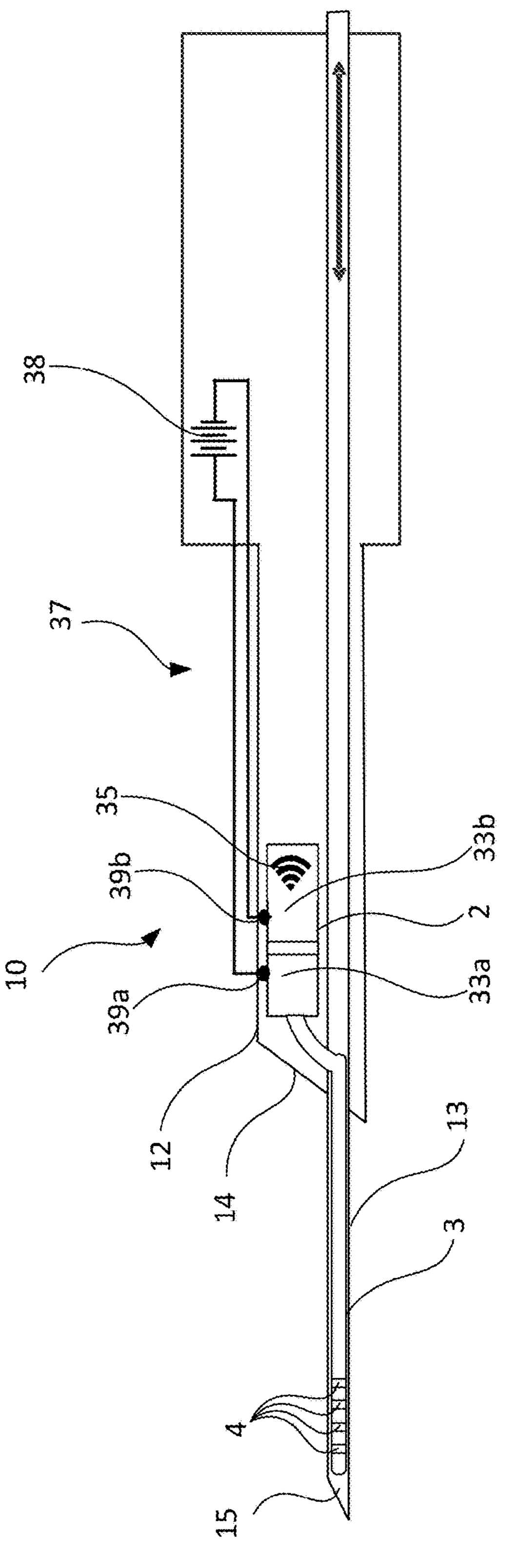
FIGS. 5A to 5C illustrate different delivery devices having first and second needles and a power delivery system.
Figure 5B:
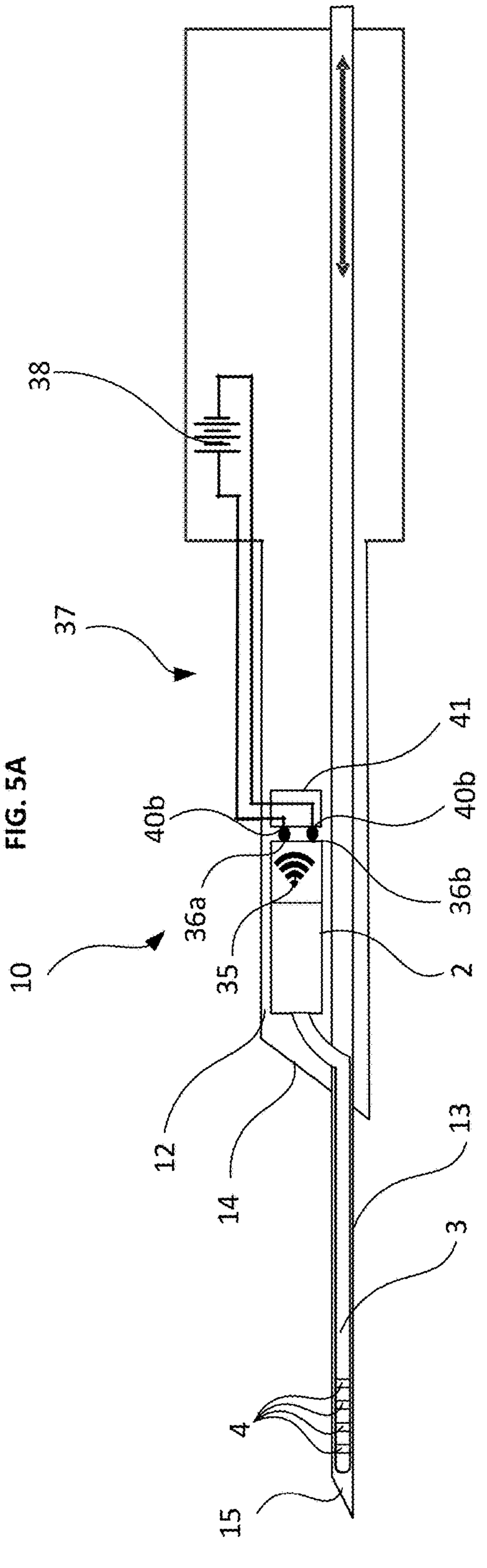
Figure 5C:
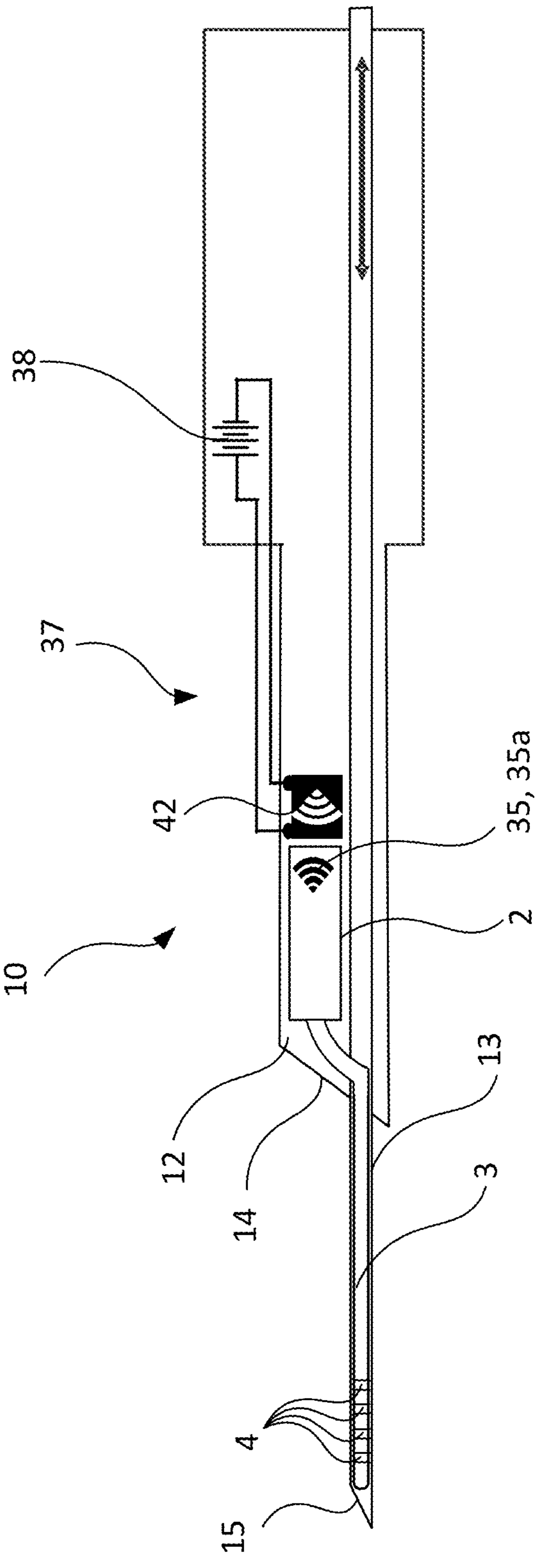

FIGS. 5A to 5C illustrate examples of delivery devices 10 for implanting the medical implants 1 illustrated in FIGS. 3A to 4B in a patient's tissue. In particular, the delivery devices 10 are used to percutaneously implant the medical implant 1 to the location shown in FIG. 2. The delivery devices 10 of FIGS. 5A to 5C are illustrated with reference to an example medical implant 1, specifically a neurostimulator implant, having a housing portion 2 and an electrode lead 3, but it will be appreciated that the delivery devices 10 may be adapted for implantation of other medical implants 1 described with reference to FIGS. 3A to 3D.

In example of FIGS. 5A to 5C, the delivery device 10 has a delivery sheath comprising a first part and a second part, specifically a first needle 12 and a second needle 13. The first and second needles 12, 13 are parallel and both extend in a longitudinal direction. The second needle 13 extends further than the first needle 12. In particular, the first needle 12 has a tip 14, such as a bevel tip, and the second needle 13 extends past the tip 14 of the first needle 12. The second needle 13 also has a tip 15, in particular a bevel tip. The second needle 13 has a higher gauge than the first needle 12 (i.e., the second needle 13 has a smaller diameter than the first needle 12).

During use, the housing portion 2 of the medical implant 1 is received in the first needle 12, in particular in a lumen of the first needle 12. During use, the electrode lead 3 is received in the second needle 13, in particular in a lumen of the second needle 13. The electrode lead 3 extends along a substantial part of the second needle 13 towards the tip as illustrated. A part of the electrode lead 3 adjacent to the housing portion 2 extends through an opening in the second needle 13, as described further with reference to FIG. 7. Accordingly, during use the medical implant 1 is housed within the first and second needles 12, 13 of the delivery device 10.

As illustrated, the first needle 12 and the second needle 13 are axially offset. In particular, a central axis of the first needle 12 is offset from a central axis of the second needle 13. In the illustrated example the second needle 13 extends into the first needle 12 (in particular into the lumen of the first needle 12), such that the second needle 13 is partly accommodated within the first needle 12 alongside the housing portion 2.

Figure 7:
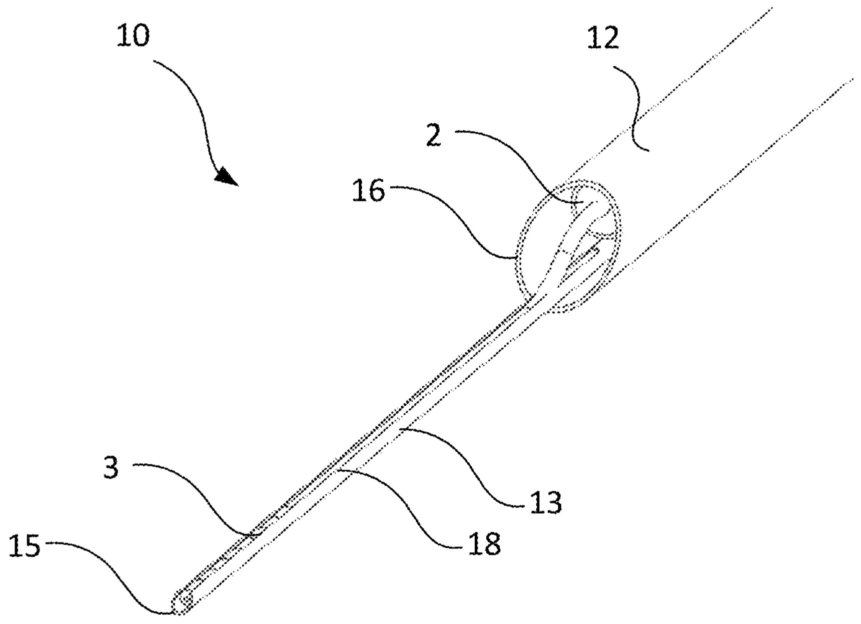
FIG. 7 illustrates the first and second needles of the delivery device of FIGS. 5A to 6C.

Referring to FIG. 7, the second needle 13 includes an opening 18, or slot, to permit a part of the electrode lead 3 to extend out of the second needle 13 and connect to the housing portion 2. The opening 18 may extend to the tip 15 of the second needle 13. The opening 18 may extend along the majority of the second needle 13, or all of the second needle 13.

Referring again to FIGS. 5A to 5C, during use the first needle 12 percutaneously penetrates the patient's tissue to position the housing portion 2 at a first depth, and the second needle 13 percutaneously penetrates the patient's tissue to position the electrode lead 3 at a second depth. Once the electrode lead 3 is correctly positioned the delivery device 10 then releases and deploys the medical implant 1 to leave the medical implant 1 in the position illustrated in FIG. 2. The tips 14, 15 of the first and second needles 12, 13, respectively, are sharp tips adapted to pierce the patient's skin and penetrate the tissue to percutaneously position the first and second needles 12, 13 at the appropriate depth. The tips 14, 15 may be bevel tips, as would be known to the skilled person. In some examples, during use the first and second needles 12, 13 are used to pierce the patient's skin and underlying tissue, and in some examples an incision is first made and the first and second needles 12, 13 are inserted through the incision into the patient's tissue.

In examples, the first needle 12 may have a gauge of between 6 gauge and 15 gauge, for example 10 gauge. In examples, the second needle 13 may have gauge of between 15 gauge and 25 gauge, for example 20 gauge.

In various examples, the second needle 13 is retractable relative to the first needle 12, to deploy the electrode lead 3. The opening 18 (see FIG. 7) along the second needle 13 permits deployment of the electrode lead 3 as the second needle 13 is retracted.

In examples, the housing portion 2 is releasably attached to the first needle 12 (or another part of the delivery device 10) and is released prior to deployment.

In examples, the housing portion 2 may be deployed from the first needle 12 simply by pulling the implant delivery device away from the patient and relying on friction between the electrode lead 3 and the patient's tissue to hold the medical implant in place and pull the housing portion 2 from the first needle 12. In other examples, the delivery device 10 may include a deployment member, such as a pusher, adapted to push the housing portion 2 out of the first needle 12 to deploy the housing portion 2 at the appropriate anatomical site. In some examples, the implant delivery device may include a retaining member arranged to hold the housing portion 2 in the first needle 12 prior to deployment, and may be operable to release the housing portion 2 before the delivery device 10 is removed.

As shown in FIGS. 5A to 5C, the delivery device 10 includes a power delivery system 37. The power delivery system 37 is arranged to provide electric power to the medical implant 1 within the delivery device 10, specifically when the housing portion 2 is received in the first needle 12 and the electrode lead 3 is received in the second needle 13. In such an arrangement the wireless power receiver (35, 35B, see FIGS. 3A to 3D) would not reliably be able to receive wireless power from the external device (32, see FIG. 2), so the power delivery system 37 is provided in the delivery device 10 to power the medical implant 1 within the delivery device 10. It may be advantageous to power the medical implant 1 within the delivery device 10 in order to test the position of the electrodes 4 during implantation, before fully deploying the medical implant 1 from the delivery device 10. In examples, to test the position of the electrodes 4 the second needle 13 is partially retracted to expose the electrodes 4, and the power delivery system 37 is operated to power the medical implant 1.

In the example of FIG. 5A the delivery device 10 is holding the medical implant 1 illustrated in FIG. 3A, with the first and second power terminals 33*a*, 33*b* formed on the housing portion 2. In this example, the power delivery system 37 includes first and second connectors 39*a*, 39*b* arranged in the first needle 12 and arranged to connect with the first and second power terminals 33*a*, 33*b* on the housing portion 2. A power source 38 (e.g., a battery or connection to an external power source (external battery or mains power)) is connected to the first and second connectors 39*a*, 39*b*. Accordingly, the medical implant 1 can be powered by the power source 38 while inside the delivery device 10. In examples, the first and second power terminals 33*a*, 33*b* are conductive areas of the casing 2*a* that extend over a portion of the length of the casing 2*a* and so the housing portion 2 may move along the first needle 12 while remaining in contact with the first and second connectors 39*a*, 39*b* on the first needle 12.

Alternatively, the delivery device 10 illustrated in FIG. 5A may be adapted to implant the medical implant 1 shown in FIG. 3D, with no electrode lead 3. In this example, the second needle 13 may be omitted, or provided only for puncturing the tissue of the patient. The first and second connectors 39*a*, 39*b* of the power delivery system 37 connect with the first and second power terminals 33*a*, 33*b* on the housing portion 2 of the medical implant 1 to power the medical implant during implantation as described above.

In the example of FIG. 5B the delivery device 10 is holding the medical implant 1 illustrated in FIG. 3B, with the first and second power terminals 36*a*, 36*b* formed at the end of the housing portion 2. In this example, the power delivery system 37 includes first and second connectors 40*a*, 40*b* arranged in the first needle 12 and arranged to connect with the first and second power terminals 36*a*, 36*b* on the end of the housing portion 2. The first and second connectors 40*a*, 40*b* of the power delivery system 37 may be provided on a contact block 41 fixed in the first needle 12. A power source 38 (e.g., a battery or connection to an external power source (external battery or mains power)) is connected to the first and second connectors 40*a*, 40*b*. Accordingly, the medical implant 1 can be powered by the power source 38 while inside the delivery device 10.

In the example of FIG. 5C the delivery device 10 is holding the medical implant 1 illustrated in any of FIGS. 3A to 3D. In these examples, the medical implant includes a wireless power receiver 35. In the specific example of FIG. 3C, the medical implant 2 includes an additional wireless power receiver 35*a*. In this example, the power delivery system 37 includes a wireless power transmitter 42 disposed in the first needle 12, behind the housing portion 2. A power source 38 (e.g., a battery or connection to an external power source (external battery or mains power)) is connected to the wireless power transmitter 42 and during operation power is wirelessly transmitted to the wireless power receiver 35, 35*a* in the medical implant 1. Accordingly, the medical implant 1 can be powered by the power source 38 while inside the delivery device 10.

Figure 6A:
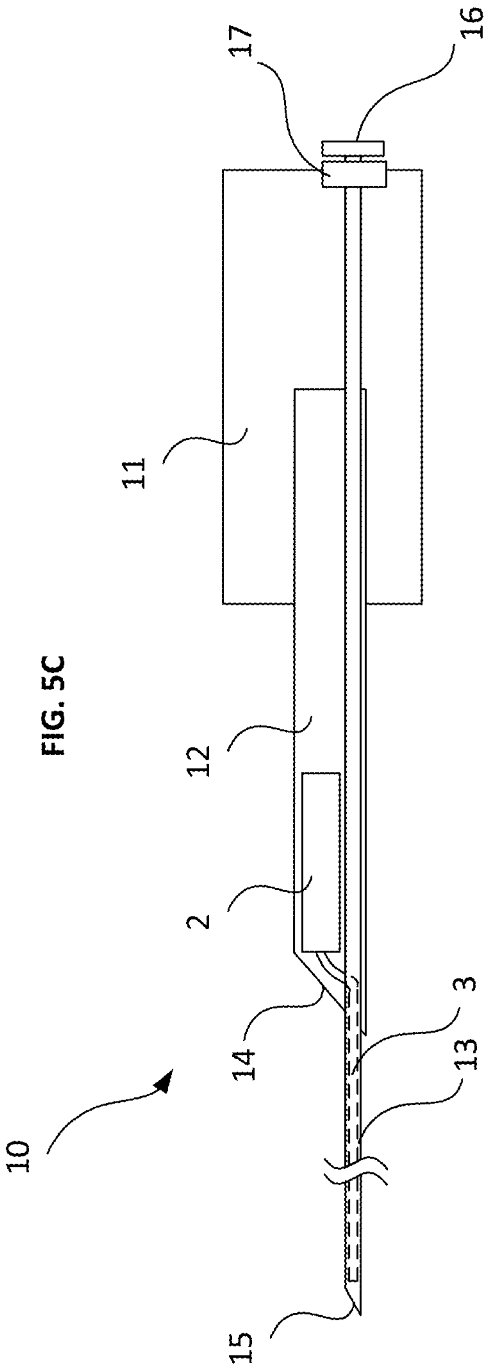
FIGS. 6A to 6C illustrate operation of an example delivery device having first and second needles.
Figure 6B:
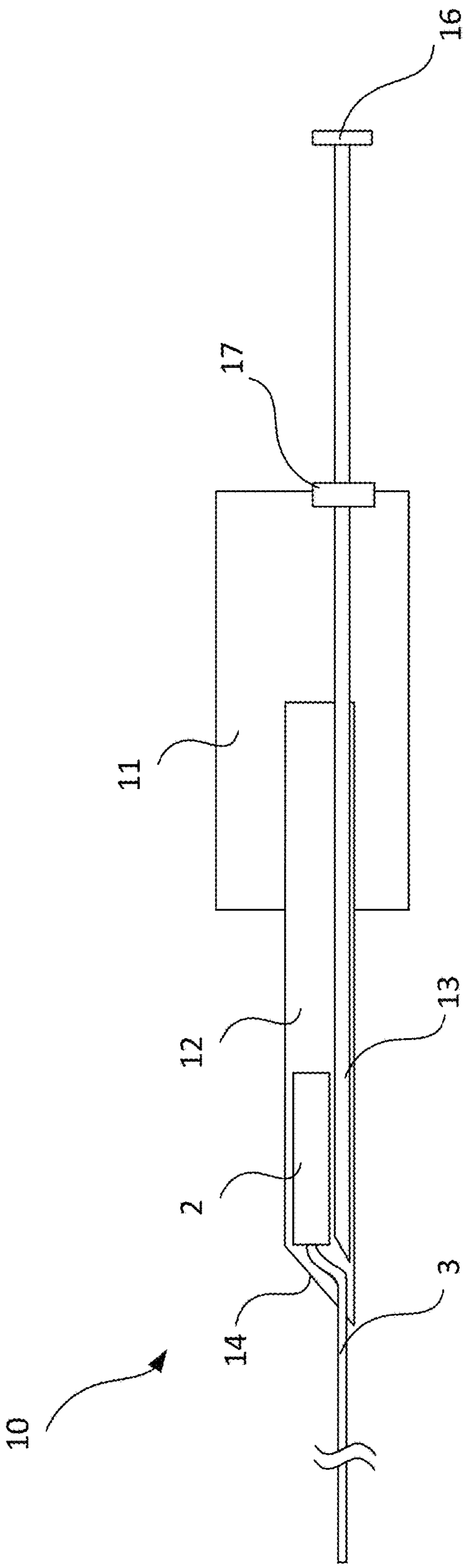
Figure 6C:
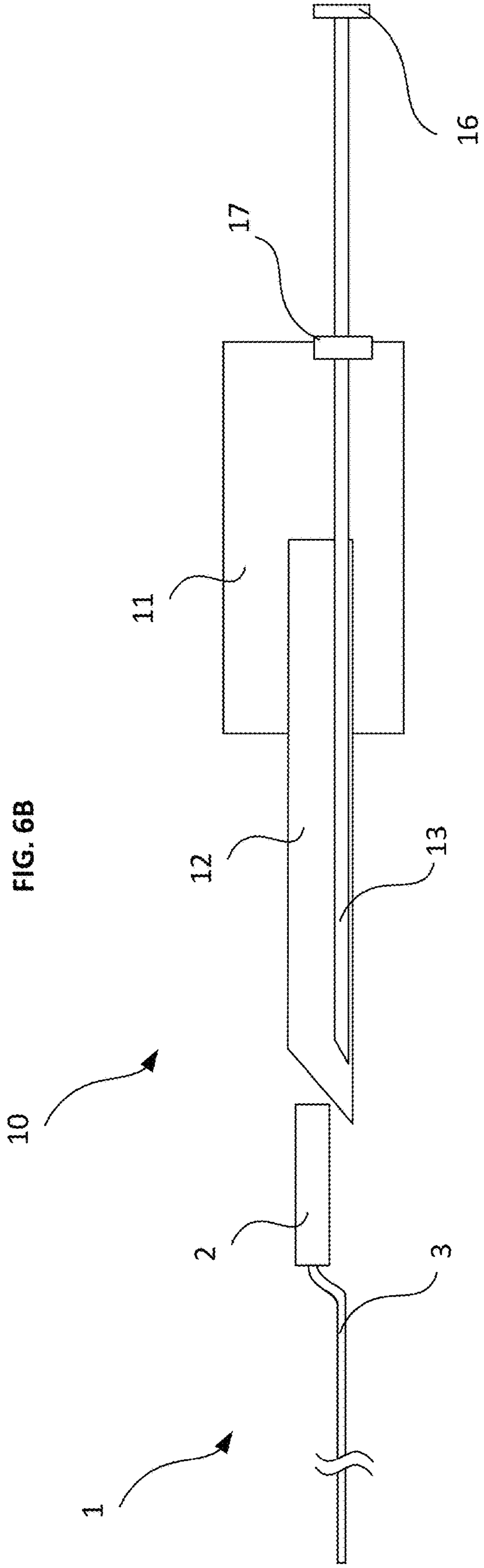

FIGS. 6A to 6C illustrate operation of the delivery device 10 of any of FIGS. 5A to 5C.

As illustrated, the example implant delivery device 10 further includes a handle 11. The handle 11 is adapted to be held by an operator. The first needle 12 is fixed to the handle 11.

The second needle 13 extends through the first needle 12 and through the handle 11. An actuation tab 16 is provided on an end of the second needle 13 opposite to the tip 15. In particular, the actuation tab 16 may be a gripping handle or similar for the operator to grip.

The second needle 13 is retractable relative to the first needle 12. In particular, the second needle 13 can slide through the first needle 12 and handle 11, from the position shown in FIG. 6A to the position shown in FIG. 6B. In this example, the second needle 13 is retractable by pulling the actuation tab 16 in a direction away from the patient. Retracting the second needle 13 in this way deploys the electrode lead 3. The opening 18 (see FIG. 7) along the second needle 13 provides for the part of the electrode lead 3 that connects to the housing portion 2. The opening 18 extends to the tip 15 of the second needle 13.

A locking device 17 is provided to lock the second needle 13 to the handle 11 and/or first needle 12. As shown, the locking device 17 may be provided at or near the actuation tab 16, and in examples locks the actuation tab 16 and/or the second needle 13 to the handle 11. The locking device 17 locks the second needle 13 in the extended position shown in FIG. 6B.

In the position shown in FIG. 6A the operator can percutaneously position the implant delivery device 10 in the patient's tissue. The position of the second needle 13 is locked relative to the handle 11, so the operator can push the implant delivery device 10 into the patient by the handle 11.

Referring to FIGS. 6A and 2, as the implant delivery device 10 is pushed into the patient the second needle 13 first penetrates the skin 5, and as the implant delivery device is pushed further the first needle 12 then penetrates the skin 5. The first and second needles 12, 13 are thereby positioned at the appropriate depths in the patient, and the housing portion 2 and electrode lead 3 are also simultaneously positioned at the appropriate depths. Therefore, the implant delivery device 10 provides percutaneous delivery of the medical implant 1 into the patient's tissue.

In examples, the operator may use an ultrasound imaging device to monitor the positions of the second needle 13 (and the first needle 12) to guide the second needle 13 towards the target nerve 9.

Once the implant delivery device 10 is in position, with the tip 15 of the second needle 13 (and the electrode lead 3 within the second needle 13) being positioned proximate to the nerve, and the tip 14 of the first needle 12 (and the housing portion 2 within the first needle 12) being positioned in the subcutaneous tissue, the second needle 13 can be partially retracted to a position between those shown in FIGS. 6A and 6B. In particular, the second needle 13 can be partially retracted to expose the electrodes (4, see FIGS. 3A to 3D). In this position the power delivery system (37, see FIGS. 5A to 5C) can power the medical implant 1 to test the position of the electrodes (4, see FIGS. 3A to 3D). If needed, the second needle 13 can be re-extended to the position shown in FIG. 6A and repositioned.

Once the electrode lead 3 is appropriately positioned, the second needle 13 is retracted to the position shown in FIG. 6B to deploy the electrode lead 3.

The second needle 13 is retracted by unlocking the locking mechanism 17 and pulling on the actuation tab 16 relative to the handle 11 to slide the second needle 13 to the retracted position shown in FIG. 6B. The actuation tab 16 is pulled in a direction away from the patient. During retraction of the second needle 13 the handle 11 and first needle 12 remain stationary. As shown, once the second needle 13 is retracted the electrode lead 3 is deployed and exposed to the surrounding tissue (and nerve).

Next, as shown in FIG. 6C, the implant delivery device 10 is withdrawn from the patient and the housing portion 2 is deployed from the first needle 12. In this example the friction between the electrode lead 3 and the tissue (see muscle 8 in FIG. 2) is enough to hold the medical implant 1 in place as the implant delivery device 10 is withdrawn, thereby deploying the housing portion 2 out of the first needle 12 as the implant delivery device 10 is withdrawn from the patient.

In other examples the implant delivery device 10 may include a deployment member (e.g., a pusher in the first needle 12) configured to push the housing portion 2 out of the first needle 12. In some examples, the implant delivery device 10 may have a retaining member arranged to releasably attach the housing portion 2 to the first needle 12 and/or handle 11, and the retaining member can release the housing portion 2 after the second needle 13 is retracted and before the first needle 12 is removed from the patient.

Figure 8A:
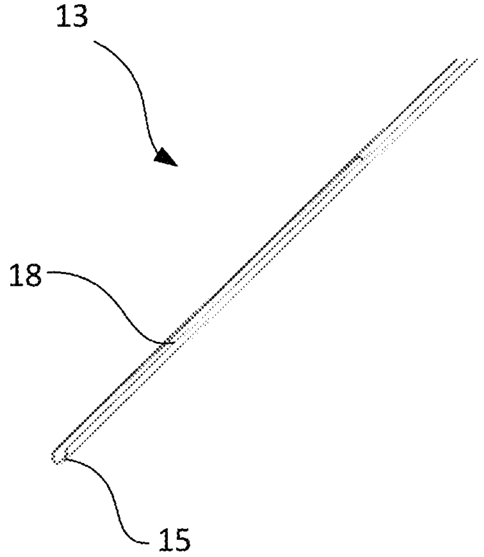
FIG. 8A illustrates the second needle of the delivery device of FIGS. 5A to 6C.
Figure 8B:
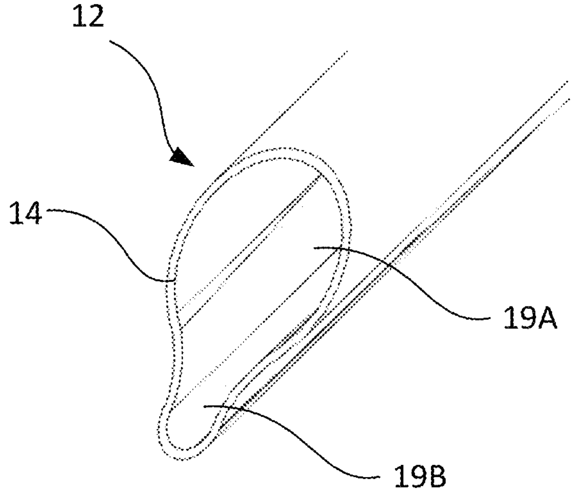
FIG. 8B illustrates the first needle of the delivery device of FIGS. 5A to 6C.

FIGS. 7, 8A and 8B illustrate the first needle 12 and the second needle 13 of the delivery device 10 described above. As shown, the electrode lead 3 is received in the second needle 13, and the second needle 13 includes a slot 18 that allows the electrode lead 3 to connect to the housing portion 2 in the first needle 12. The slot 18 extends partially along the second needle 13 from the tip 15, and may extend the majority of the length of the second needle 13, or the entire length of the second needle 13. The second needle 13 may be in the form of a sheath. The first needle 12 receives the housing portion 2.

The first needle 12 includes a bevel tip 14. The second needle 13 includes a bevel tip 15. The bevel tips 14, 15 are sharp for piercing a patient's skin and penetrating the tissue during use.

As shown in FIG. 7, the second needle 13 extends through the lumen of the first needle 12. In particular, as shown in FIG. 8B the first needle 12 includes a primary portion 19A and a secondary portion 19B. The primary and secondary portions 19A, 19B are merged such that the first needle 12 has a single lumen. The primary and secondary portions 19A, 19B are shaped to define the two distinct portions 19A, 19B.

The primary portion 19A is shaped to receive the housing portion 2. In particular, the primary portion 19A is sized to receive the housing portion 2 and has a substantially circular cross-section that retains the housing portion 2 in axial alignment within the primary portion 19A.

The secondary portion 19B is shaped to receive the second needle 13. In particular, the secondary portion 19B is sized to receive the second needle 13 and has a substantially circular cross-section that retains the second needle 13 in axial alignment within the secondary portion 19B.

In examples, the secondary portion 19B and the primary portion 19A each have a substantially circular cross-section, and the cross-sections at least partially overlap. In such an example, the housing portion may be pushed over to one side of the primary portion 19A by the presence of the second needle 13 in the secondary portion 19B.

The slot 18 in the second needle 13 is directed towards the centre of the first needle 12, allowing the electrode lead 3 to connect with the housing portion 2 as shown in FIG. 7.

Accordingly, the first needle 12 is shaped to receive the housing portion 2 and the second needle 13, and to permit the second needle 13 to slide towards the retracted position. The position of the second needle 13 within the lumen of the first needle 1 beneficially means that there is only one puncture wound formed in the patient's skin, as the first needle 12 will enlarge the puncture wound formed by the second needle 13 during use.

In alternative examples the second needle 13 does not pass into, or through, the lumen of the first needle 12. Instead, the second needle 13 can extend through another part of the handle 11, for example adjacent to the first needle 12.

Figure 9:
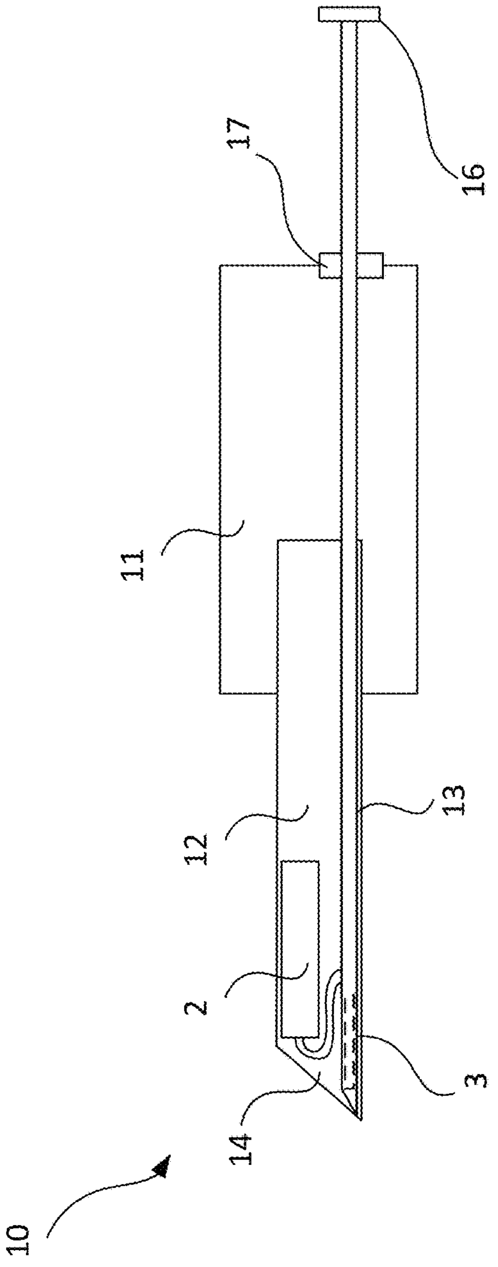
FIG. 9 illustrates an alternative delivery device with the second needle in an initially retracted position.

In the above-described examples the second needle 13 is initially in an extended position, and the first and second needles 12, 13 can be simultaneously positioned in the patient. FIG. 9 illustrates an alternative example in which the second needle 13 is initially in a retracted position. In this example, as shown, the actuation tab 4 extends from the handle 11. In the retracted position the second needle 13 may be within the first needle 12, as illustrated, or alongside the first needle 12 within the handle 11. The electrode lead 3 is partially within the second needle 13 and looped between the housing portion 2 and the second needle 13.

During implantation, the first needle 12 is inserted into the patient with the implant delivery device 10 in the configuration shown in FIG. 9, then the actuation tab 16 is pushed towards the handle 11 to extend the second needle 13 beyond the first needle 12 and carry the electrode lead 3 into position. In this position the locking mechanism 17 can be engaged such that the actuation tab 16 and second needle 13 are locked in position.

In some examples, the implant delivery device 10 may be removed from the patient with the second needle 13 in the extended position, and a deployment member (e.g., a pusher) may be provided to urge the medical implant 1 out of the first and second needles 12, 13. In other examples, after being extended the second needle 13 can then be retracted by pulling the actuation tab 16 away from the handle 11 in the manner described above with reference to FIGS. 6A to 6C, to release the electrode lead 3 and housing portion 2.

Figure 10:
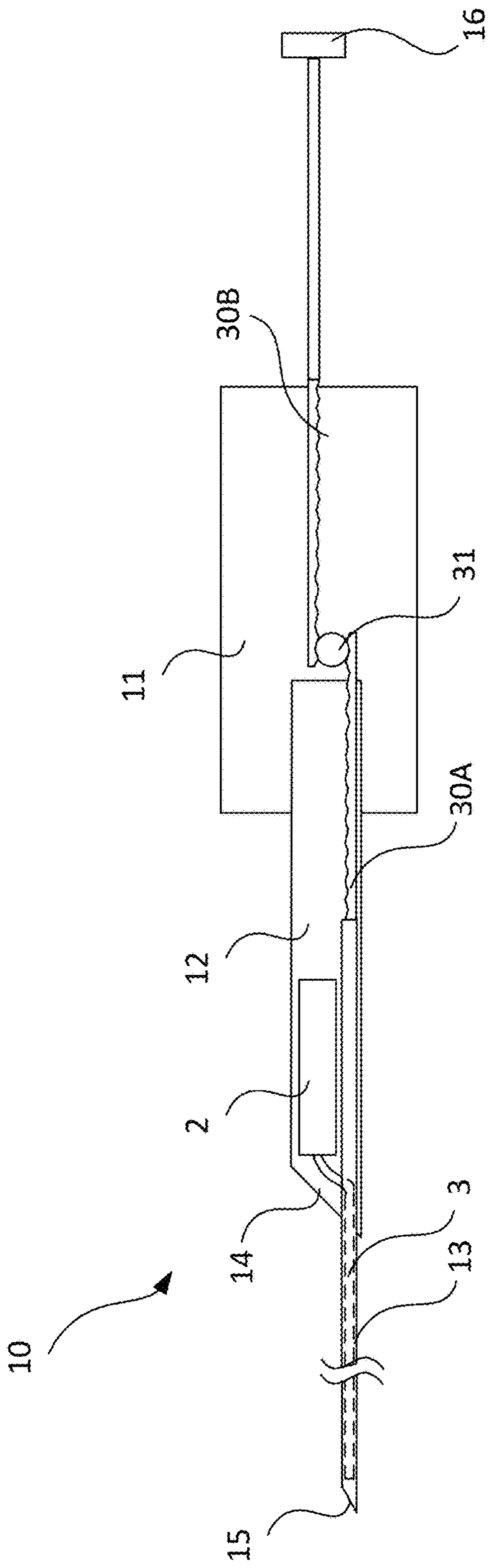
FIG. 10 illustrates an alternative delivery device with a rack and pinion arrangement.

FIG. 10 illustrates an alternative example delivery device 10. In this example the delivery device 10 comprises a handle 11, a first needle 12 holding the housing portion 2 and a second needle 13 holding the electrode lead 3, as previously described. In this example, the actuation tab 16 is arranged to be pushed towards the handle 11 (and the patient) in order to retract the second needle 13.

In particular, as illustrated, the implant delivery device 10 has a rack and pinion mechanism for translating movement of the actuation tab 16 towards the handle 11 into retraction of the second needle 13 (i.e., the second needle 13 moves in an opposite direction to the actuation tab 16).

As shown in FIG. 10, the rack and pinion mechanism comprises a first rack portion attached to, or formed as part of, the second needle 13. The rack and pinion mechanism also comprises a second rack portion 30B attached to, or formed as part of, the actuation tab 16. A pinion gear 31 is rotatably mounted within the handle 11 and is engaged with both the first and second rack portions 30A, 30B. The pinion gear 31 may be mounted within the first needle 12 or, as illustrated, behind the end of the first needle 12 within the handle 11. Accordingly, as the actuation tab 16 is pushed towards the patient the rack and pinion mechanism causes the second needle 13 to be retracted away from the patient to release the electrode lead 3.

Advantageously, pushing the actuation tab 16, rather than pulling the actuation tab 16, may permit one-handed operation of the implant delivery device 10.

FIGS. 11A to 11D illustrate further examples of delivery devices 10 that include a power delivery system 37 similar to as described above. In particular, FIGS. 11A to 11D illustrate a delivery system 10 with a delivery sheath that comprises cannula 53 that holds the medical implant 1 before and during implantation. The entire medical implant 1, which may be any of the medical implants 1 described with reference to FIGS. 3A to 3D, is held within the cannula 53. The cannula 53 can be percutaneously positioned and the medical implant 1 can be deployed from the cannula 53, for example by a pusher 54 as illustrated.

Figure 11A:
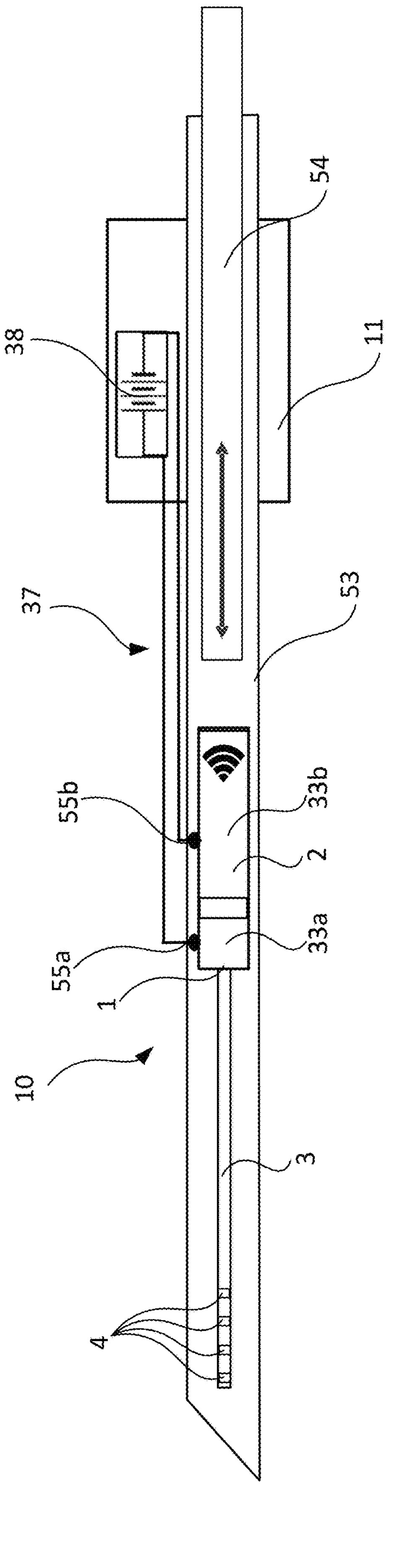
FIGS. 11A to 11D illustrate example delivery devices having a cannula and a power delivery system.

In the example of FIG. 11A, the delivery system 10 is adapted to implant the medical implant 1 described with reference to FIG. 3A, in which the housing portion 2 comprises first and second power terminals 33*a*, 33*b* formed on the side wall. As illustrated, the power delivery system 37 comprises first and second connectors 55*a*, 55*b* arranged in the cannula 53 and arranged to connect with the first and second power terminals 33*a*, 33*b* on the housing portion 2. The first and second connectors 55*a*, 55*b* allow the medical implant 1 to slide a small distance within the cannula 53 while maintaining electrical contact, allowing the medical implant 1 to be partially pushed out of the cannula 53 to expose the electrodes 4 before the power delivery system 37 is operated to test the position of the electrode lead 3 as described above. In particular, as the first and second power terminals 33*a*, 33*b* on the housing portion 2 of the medical implant 1 extend along a portion of the length of the housing portion 2, the housing portion 2 can move along the cannula 53 and the electrical contact will be maintained. A power source 38 (e.g., a battery or connection to an external power source (external battery or mains power)) is connected to the first and second connectors 55*a*, 55*b*. Accordingly, the medical implant 1 can be powered by the power source 38 while inside the delivery device 10.

Alternatively, the delivery device 10 illustrated in FIG. 11A may be adapted to implant the medical implant 1 shown in FIG. 3D, with no electrode lead 3. In this example, the first and second connectors 55*a*, 55*b* of the power delivery system 37 connect with the first and second power terminals 33*a*, 33*b* on the housing portion 2 of the medical implant 1 to power the medical implant 1 during implantation as described above.

Figure 11B:
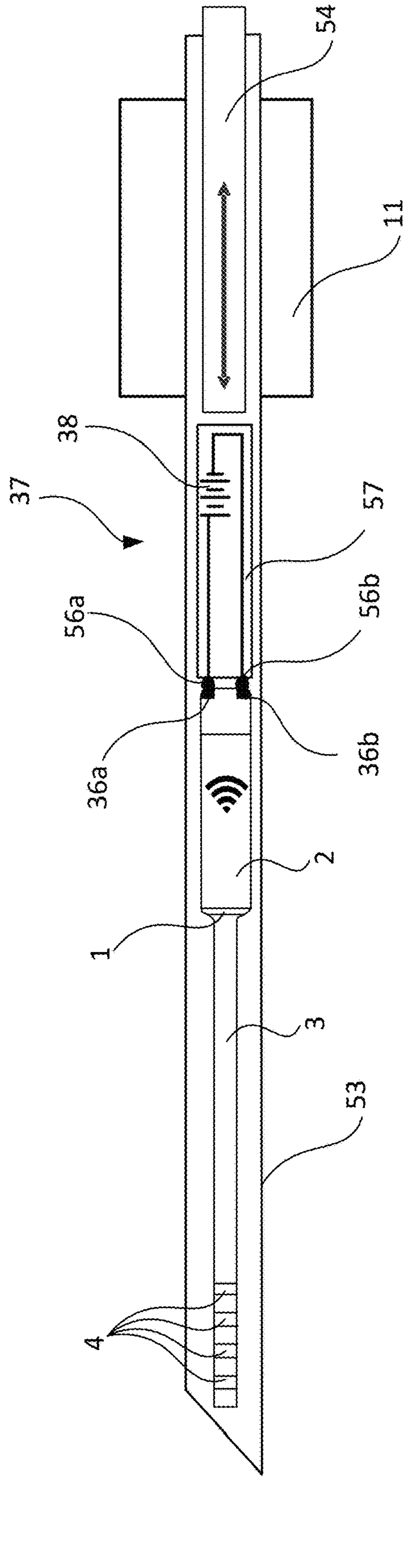

In the example of FIG. 11B, the delivery system 10 is adapted to implant the medical implant 1 described with reference to FIG. 3B, in which the housing portion 2 comprises first and second power terminals 36*a*, 36*b* formed at the end. As illustrated, the power delivery system 37 comprises first and second connectors 56*a*, 56*b* arranged in the cannula 53 and arranged to connect with the first and second power terminals 36*a*, 36*b* on the housing portion 2. A power source 38 (e.g., a battery or connection to an external power source (external battery or mains power)) is connected to the first and second connectors 56*a*, 56*b*. Accordingly, the medical implant 1 can be powered by the power source 38 while inside the delivery device 10. In this example, the power source 38 and first and second connectors 56*a*, 56*b* are formed on a mount 57 that is slidably movable within the cannula 53. In this way, the pusher 54 can push the mount 57 and medical implant 1 towards the outlet of the cannula 53 and the power connection between the first and second power terminals 36*a*, 36*b* and the first and second connectors 56*a*, 56*b* will be maintained. Alternatively, the mount 57 may be fixed within the cannula 53 and the pusher 54 may pass through or around the mount 57 to contact the housing portion 2 of the medical implant 1.

Figure 11C:
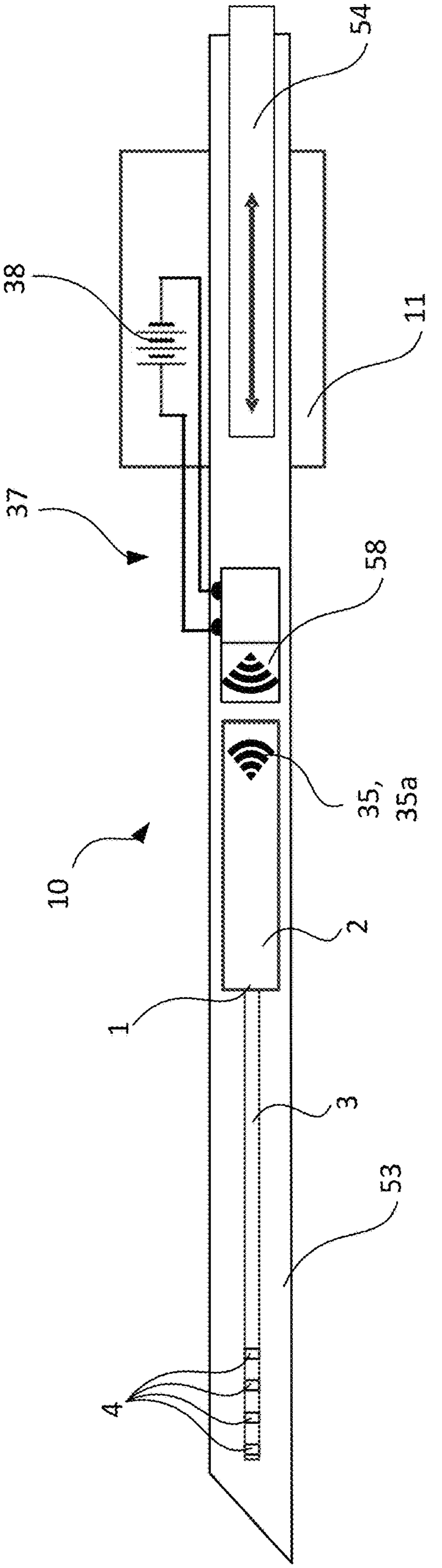

In the example of FIG. 11C, the delivery system 10 is adapted to implant the medical implant 1 described with reference to FIG. 3C, in which the housing portion 2 comprises a wireless power receiver 35*a*. Additionally or alternatively, the delivery system of FIG. 11C may be used with a medical implant having a single wireless power receiver 35, without any additional connectors or the like.

As shown in FIG. 11C the power delivery system 37 comprises a wireless power transmitter 58 arranged within the cannula 53 to wirelessly couple with the wireless power receiver 35, 35*a* of the medical implant 1. The wireless power transmitter 58 is connected to a power source 38, which may be located outside of the cannula 53, for example in the handle 11. In examples, the wireless power transmitter 58 may be coupled to the power source 38 by electrical connectors 59*a*, 59*b* that permit the wireless power transmitter 58 to slide a small distance within the cannula 53 such that the medical implant 1 can be partially pushed out of the cannula 53 to expose the electrodes 4 before the power delivery system 37 is operated to test the position of the electrode lead 3 as described above. Alternatively, the wireless power transmitter 58 may be fixed within the cannula 53 and the pusher 5 may pass through or around the wireless power transmitter 58 to contact the housing portion 2 of the medical implant 1. The power source 38 may be a battery or a connection to an external power source (external battery or mains power). Accordingly, the medical implant 1 can be powered by the power source 38 while inside the delivery device 10.

Figure 11D:
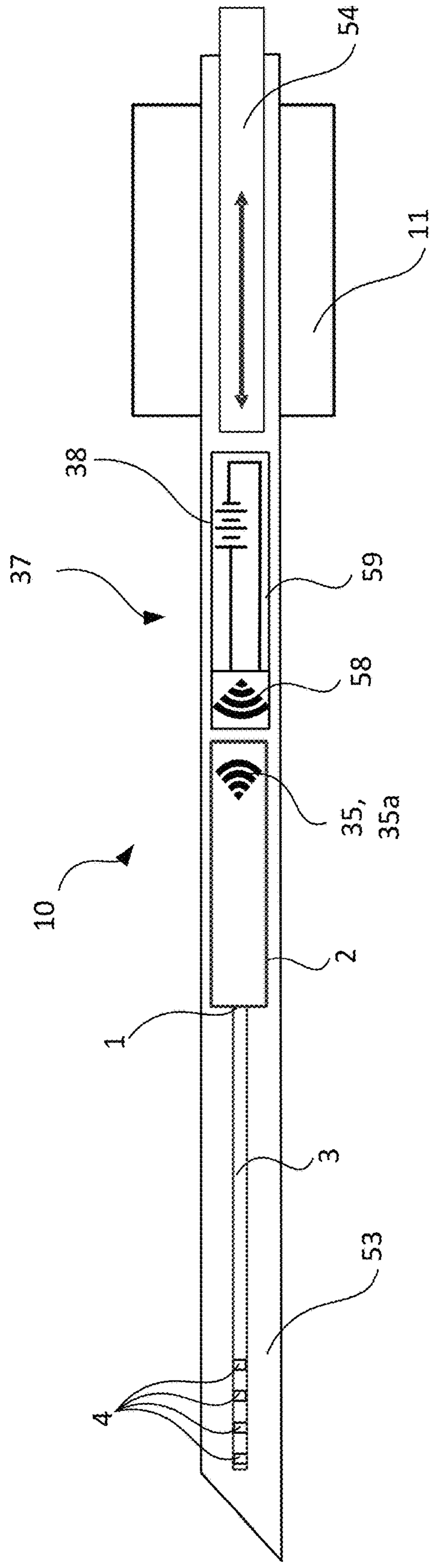

In the example of FIG. 11D, the delivery system 10 is adapted to implant the medical implant 1 described with reference to FIG. 3C, in which the housing portion 2 comprises a wireless power receiver 35*a*. Additionally or alternatively, the delivery system of FIG. 11D may be used with a medical implant having a single wireless power receiver without any additional connectors or the like.

As shown in FIG. 11D the power delivery system 37 comprises a wireless power transmitter 58 arranged within the cannula 53 to wirelessly couple with the wireless power receiver 35, 35*a* of the medical implant 1. The wireless power transmitter 58 is connected to a power source 38. The power source 38 may be a battery or a connection to an external power source (external battery or mains power). In this example, the power source 38 and the wireless power transmitter 58 are formed on a slidable mount 59 that is slidably movable within the cannula 53. In this way, the pusher 54 can push the slidable mount 59 and medical implant 1 towards the outlet of the cannula 53 and the wireless power connection can be maintained. In this way, the electrodes 4 can be exposed and the medical implant 1 can be powered to test the position of the electrode lead 3 before deployment.

In some examples, the cannula 53 as described with reference to FIGS. 11A to 11D may be a needle, for example with a bevel tip.

Figure 12A:
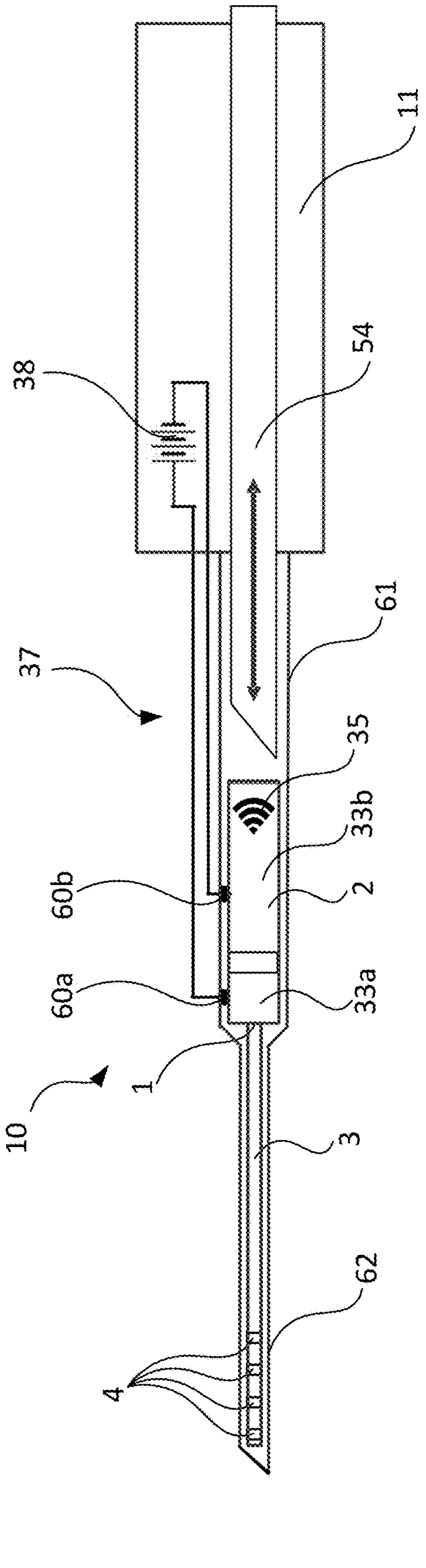
FIGS. 12A to 12C illustrate example delivery devices having a delivery sheath with first and second portions, and a power delivery system.
Figure 12B:
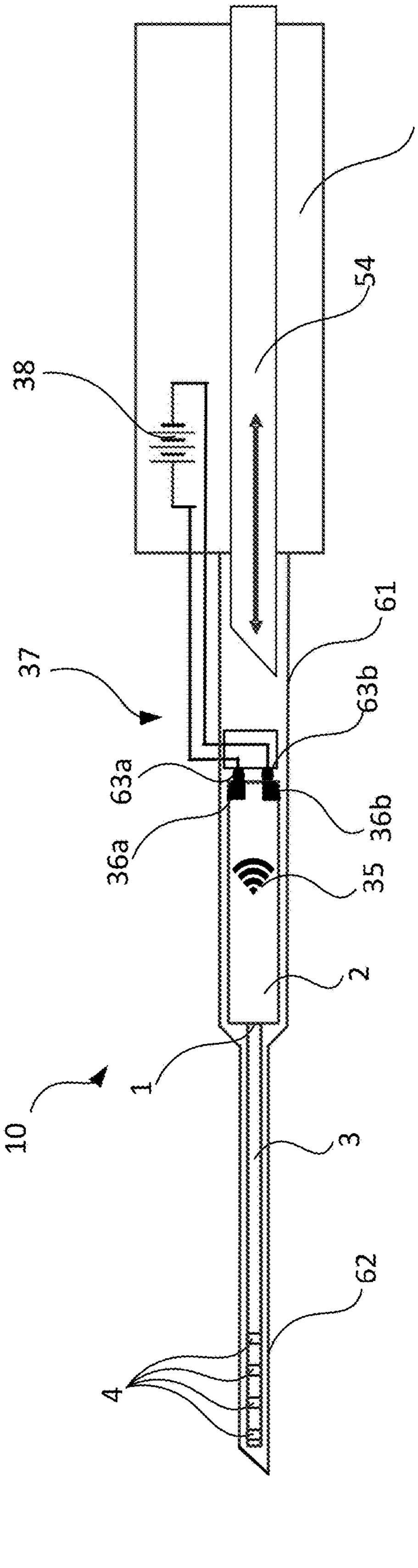
Figure 12C:
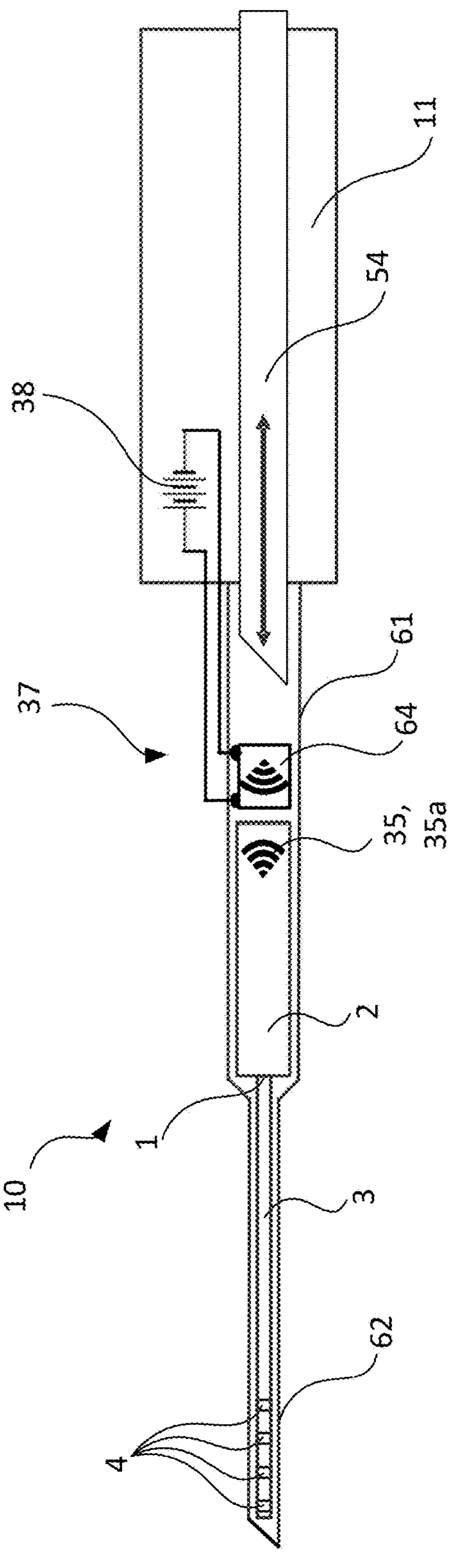

FIGS. 12A to 12C illustrate further examples of delivery devices 10 that include a power delivery system 37 as described above. In particular, FIGS. 12A to 12D illustrate a delivery system 10 having a delivery sheath that comprises a wedge-shaped needle. The wedge-shaped needle has a first portion 61 that holds the housing portion 2 of the medical implant 1, and a second portion 62 protruding from the first portion 61 and holding the electrode lead 3. The first and second portions 61, 62 are fixed to one another and have different diameters (the second portion 62 being smaller than the first portion 61). The second portion 62 includes a slot extending along its length, from the first portion 61 to its tip. The first portion 61 also has a slot or opening in the side, aligned with the slot of the second portion 62. In this way, the medical implant 1 can be deployed by a pusher 54 pushing the housing portion 2 out of the first portion 61 via the slot or opening, and the delivery device 10 can be retracted to fully implant the medical implant 1.

In example of FIG. 12A the delivery system 10 is adapted to implant the medical implant 1 described with reference to FIG. 3A, in which the housing portion 2 comprises first and second power terminals 33*a*, 33*b* formed on the side wall. As illustrated, the power delivery system 37 comprises first and second connectors 60*a*, 60*b* arranged in the first portion 61 of the delivery system 10 and arranged to connect with the first and second power terminals 33*a*, 33*b* on the housing portion 2. The first and second connectors 60*a*, 60*b* allow the medical implant 1 to slide a small distance within the first portion 61 while maintaining electrical contact, allowing the electrode lead 3 to be partially pushed out of the second portion 62 to expose the electrodes 4 before the power delivery system 37 is operated to test the position of the electrode lead 3 as described above. In particular, as the first and second power terminals 33*a*, 33*b* on the housing portion 2 of the medical implant 1 extend along a portion of the length of the housing portion 2, the housing portion 2 can move along the first portion 61 and the electrical contact will be maintained. A power source 38 (e.g., a battery or connection to an external power source (external battery or mains power)) is connected to the first and second connectors 60*a*, 60*b*. Accordingly, the medical implant 1 can be powered by the power source 38 while inside the delivery device 10.

Alternatively, the delivery device 10 illustrated in FIG. 12A may be adapted to implant the medical implant 1 shown in FIG. 3D, with no electrode lead 3. In this example, the second portion 62 may be omitted, or provided only for puncturing the tissue of the patient. The first and second connectors 60*a*, 60*b* of the power delivery system 37 connect with the first and second power terminals 33*a*, 33*b* on the housing portion 2 of the medical implant 1 to power the medical implant 1 during implantation as described above.

In the example of FIG. 12B, the delivery system 10 is adapted to implant the medical implant 1 described with reference to FIG. 3B, in which the housing portion 2 comprises first and second power terminals 36*a*, 36*b* formed at the end. As illustrated, the power delivery system 37 comprises first and second connectors 63*a*, 63*b* arranged in the first portion 61 and arranged to connect with the first and second power terminals 36*a*, 36*b* on the housing portion 2. A power source 38 (e.g., a battery or connection to an external power source (external battery or mains power)) is connected to the first and second connectors 63*a*, 63*b*. Accordingly, the medical implant 1 can be powered by the power source 38 while inside the delivery device 10. In this example, the first and second connectors 63*a*, 63*b* are formed on a mount that is slidably movable within the first portion 61. In this way, the pusher 54 can push the mount and medical implant 1 towards the opening in the first portion and the power connection between the first and second power terminals 36*a*, 36*b* and the first and second connectors 63*a*, 63*b* will be maintained. Alternatively, the mount may be fixed within the first portion 61 and the pusher 54 may pass through or around the mount to contact the housing portion 2 of the medical implant 1.

In the example of FIG. 12C, the delivery system 10 is adapted to implant the medical implant 1 described with reference to FIG. 3C, in which the housing portion 2 comprises a wireless power receiver 35*a*. Additionally or alternatively, the delivery system of FIG. 12C may be used with a medical implant 1 having a single wireless power receiver without any additional connectors or the like.

As shown in FIG. 12C the power delivery system 37 comprises a wireless power transmitter 64 arranged within the first portion 61 to wirelessly couple with the wireless power receiver 35, 35*a* of the medical implant 1. The wireless power transmitter 64 is connected to a power source 38. In this example the power source 38 is located in the handle 11. The power source 38 may be a battery or a connection to an external power source (external battery or mains power). Accordingly, the medical implant 1 can be powered by the power source 38 while inside the delivery device 10. The wireless power transmitter 64 may be moved by the pusher 54 during deployment of the medical implant 1, or it may be shaped to permit the pusher 54 to pass through or around the wireless power transmitter 64 within the first portion 61 to contact the housing portion 2 of the medical implant 1.

Figure 13A:
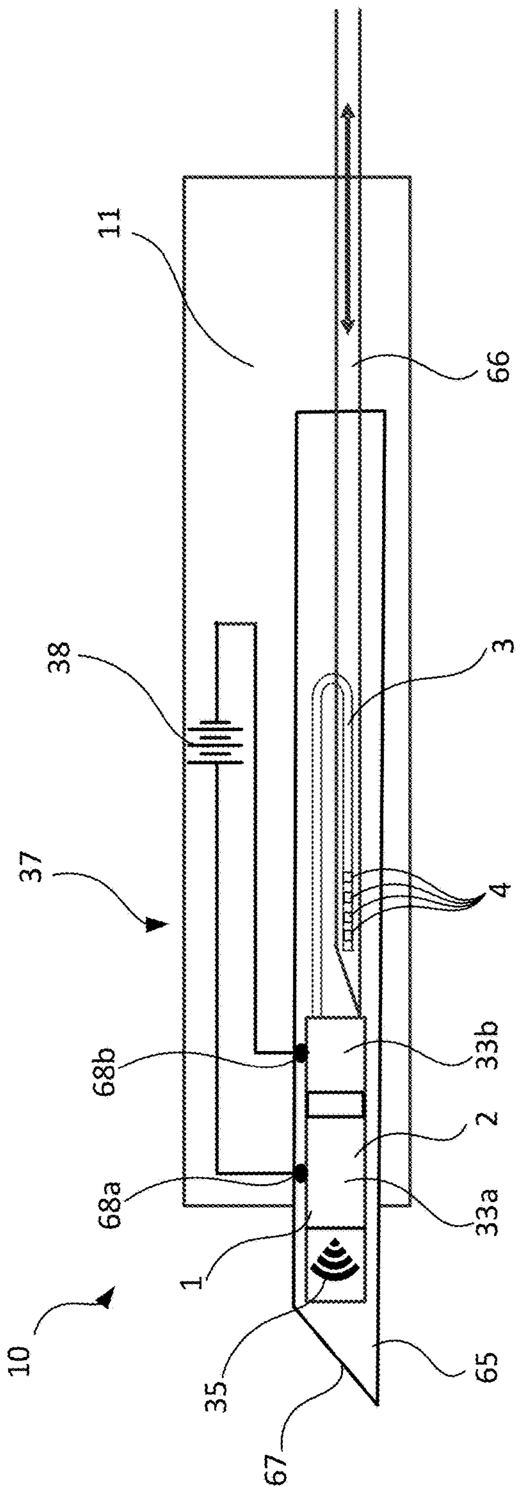
FIGS. 13A and 13B illustrate example delivery devices operable to deliver the medical implant in a reverse orientation, and having a power delivery system.
Figure 13B:
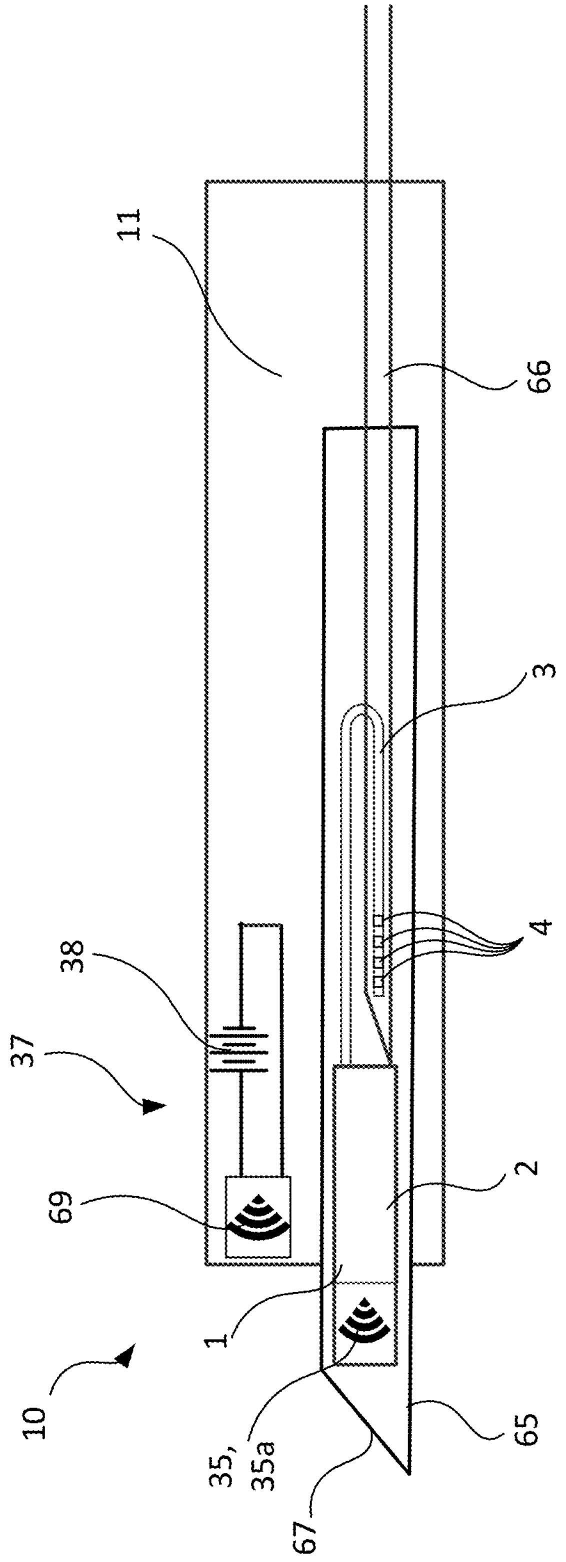

FIGS. 13A and 13B illustrate further examples of delivery devices 10 that include a power delivery system 37 as described above. In particular, FIGS. 13A to 13B illustrate a delivery system 10 that is used to first implant the housing portion 2 of the medical implant 1, and then the electrode lead 3. As illustrated, this delivery system 10 has a delivery sheath that comprises a first needle 65 that holds the housing portion 2 of the medical implant 1, and a second needle 66 that holds the electrode lead 3. The second needle 66 is extendible and retractable relative to the first needle 65 in the manner described with reference to FIGS. 6A to 6C. The housing portion 2 is oriented within the first needle 65 so that the electrode lead 3 is directed away from the tip 67 of the first needle 65. The electrode lead 3 is looped and received in the second needle 66, which has a slot 18 like that illustrated in FIG. 7. During use, the first needle 65 is percutaneously positioned to deploy the housing portion 2 and a pusher (not illustrated) or the second needle 66 is used to at least partially deploy the housing portion 2 through the tip 67. Once the housing portion 2 has been at least partially deployed the second needle 66 can be extended to deploy the electrode lead 3. The second needle 66 can then be retracted to leave the electrode lead 3 in place. During implantation, to test the position of the electrode lead 3 the second needle 66 can be partially retracted to expose the electrodes 4, and the power delivery system 37 can be operated to power the medical implant 1.

In the example of FIG. 13A the delivery system 10 is adapted to implant the medical implant 1 described with reference to FIG. 3A, in which the housing portion 2 comprises first and second power terminals 33*a*, 33*b* formed on the casing of the housing portion 2. As illustrated, the power delivery system 37 comprises first and second connectors 68*a*, 68*b* arranged in the first needle 65 of the delivery system 10 and arranged to connect with the first and second power terminals 33*a*, 33*b* on the housing portion 2. The first and second connectors 68*a*, 68*b* allow the medical implant 1 to slide a small distance within the first needle 66 while maintaining electrical contact, allowing the housing portion 2 to be partially pushed out of the first needle 65 before the power delivery system 37 is operated to test the position of the electrode lead 3 as described above. In particular, as the first and second power terminals 33*a*, 33*b* on the housing portion 2 of the medical implant 1 extend along a portion of the length of the housing portion 2, the housing portion 2 can move along the first needle 65 and the electrical contact will be maintained. A power source 38 (e.g., a battery or connection to an external power source (external battery or mains power)) is connected to the first and second connectors 68*a*, 68*b*. Accordingly, the medical implant 1 can be powered by the power source 38 during implantation.

Alternatively, the delivery device 10 illustrated in FIG. 13A may be adapted to implant the medical implant 1 shown in FIG. 3D, with no electrode lead 3. In this example, the second needle 66 may be omitted, or provided only for puncturing the tissue of the patient. The first and second connectors 68*a*, 68*b* of the power delivery system 37 connect with the first and second power terminals 33*a*, 33*b* on the housing portion 2 of the medical implant 1 to power the medical implant 1 during implantation as described above.

In the example of FIG. 13B, the delivery system 10 is adapted to implant the medical implant 1 described with reference to FIG. 3C, in which the housing portion 2 comprises a wireless power receiver 35*a*. Additionally or alternatively, the delivery system 10 of FIG. 13B may be used with a medical implant having a single wireless power receiver 35, without any additional connectors or the like.

As shown in FIG. 13B the power delivery system 37 comprises a wireless power transmitter 69 arranged within handle 11 to wirelessly couple with the wireless power receiver 35, 35*a* of the medical implant 1. The wireless power transmitter 69 is connected to a power source 38. In this example the power source 38 is located in the handle 11. The power source 38 may be a battery or a connection to an external power source (external battery or mains power). Accordingly, the medical implant 1 can be powered by the power source 38 while inside the delivery device 10.

Figure 14:
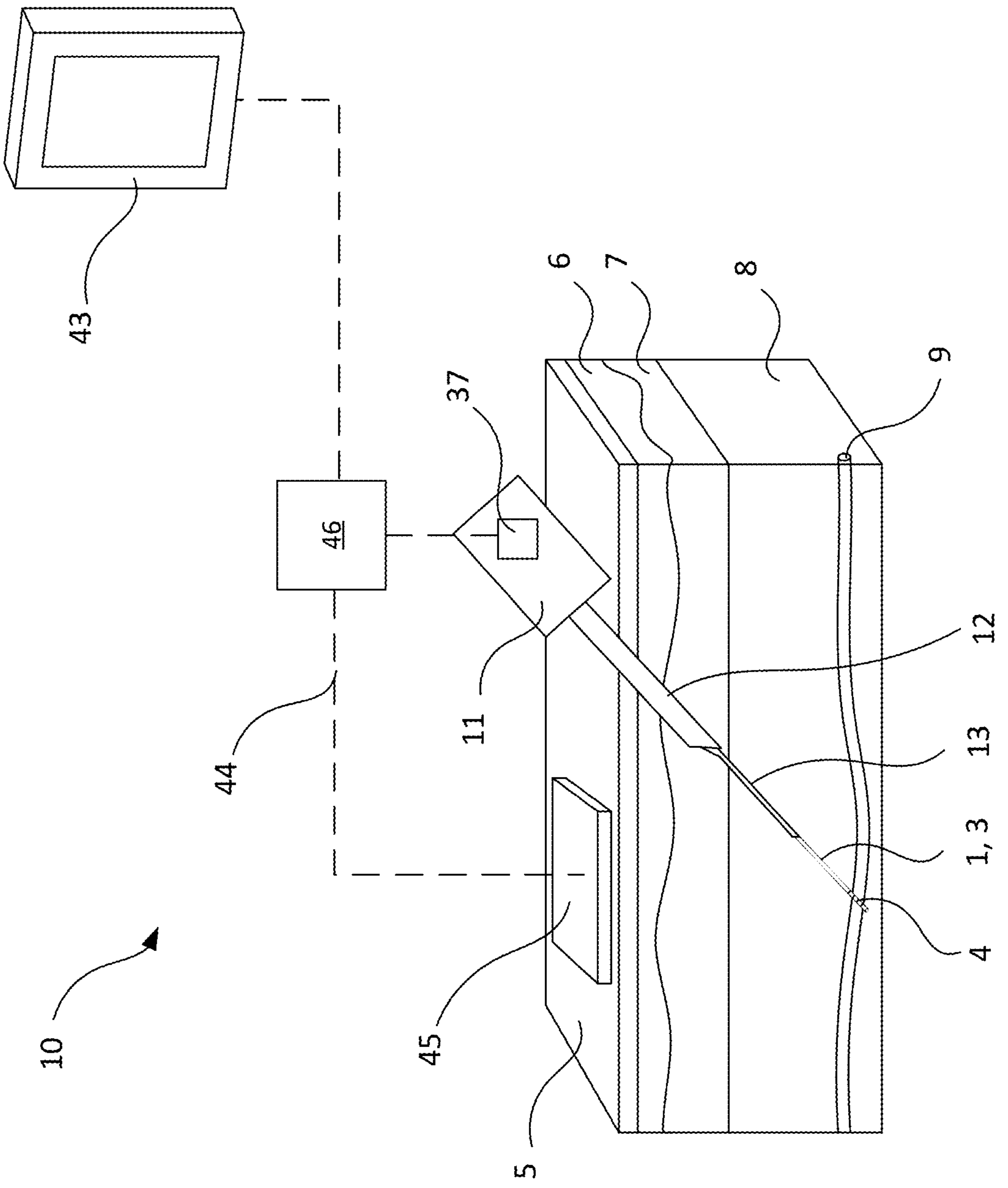
FIG. 14 illustrates operation of the delivery device to test a position of the medical implant during implantation.

FIG. 14 illustrates testing of the medical implant 1 during implantation using any of the delivery devices 10 described above with reference to FIGS. 5A to 13B. Each example delivery device 10 includes a delivery sheath that holds the medical implant 1, and a power delivery system 37 for powering the medical implant 1 within the delivery sheath. FIG. 14 illustrates the specific example delivery device 10 of FIGS. 3A to 9, but it will be appreciated that the same testing process can be used for any of the delivery devices 10 described herein.

As shown in FIG. 14, the delivery sheath (in this example the first and second needles 12, 13) have been percutaneously positioned through the patient's skin 5 and into the tissue 8. The electrodes 4 (in this example on the electrode lead 3) have been guided close to the nerve 9, for example using an ultrasound scanner. The electrodes 4 have been exposed, in this example by partly retracting the second needle 13. In this position the power delivery system 37 can be operated to power medical implant 1 and test the location of the electrodes 4 relative to the nerve 9.

In some examples the medical implant 1 is a neurostimulator implant operable to stimulate the nerve 9 by providing electrical signals through the electrodes 4. In this example, the position of the neurostimulator implant may be tested to ensure that the electrical signals provided by the electrodes 4 have the desired effect on the nerve 9.

In some examples, the operator may use visual or patient feedback to determine whether the medical implant 1 is having the desired effect. For example, if the medical implant 1 is being used to address sleep apnea then a visual feedback may include tongue position (e.g., a degree at which the tongue is protruding). Other forms of visual or patient feedback may include a patient touch test (to test sensation) or patient feedback on pain severity/tingling sensation. In one example the medical implant 1 may be implanted to address a urinary indication, in which case visual feedback may be provided by the passing of urine.

As shown in FIG. 14, the delivery device 10 may include a sensor 45. In the illustrated example the sensor 45 is attachable to the patient, in particular the patient's skin 5. The sensor may be adhered to the skin 5, or otherwise held in place, for example by a strap or as a wearable. In other examples, the sensor 45 may be provided in the delivery device 10 itself, for example in the handle 11. In other examples, the sensor 45 may be provided in a wearable device that accompanies the neurostimulator implant, for example a wearable that provides wireless power and control after implantation is completed. In some examples, the sensor 45 may be provided in the medical implant 1.

The sensor 45 is provided to detect a reaction of the patient when power is provided to the neurostimulator implant 1 during implantation. In some examples, the sensor 45 may detect a movement reaction of the patient in response to testing of the neurostimulator implant 1. The movement reaction may be detected by an accelerometer (e.g., a Micro Electro-Mechanical System, MEMS, sensor), or by an electromyography, EMG, sensor, or by an ultrasonic sensor. In other examples, the sensor 45 may detect a change in blood flow of the patient, for example using an ultrasonic sensor or other blood flow sensor. In some examples, the sensor 45 may be a bioimpedance-impedance blood pressure sensor and may integrated into the electrodes 4 of the medical implant 1. In some examples, the sensor may be a radar-based blood pressure sensor. In some examples, the sensor 45 may detect the position of the body part. For example, if treating sleep apnea then the sensor 45 may detect a position of the tongue.

In some examples the medical implant is a diagnostic implant 1 operable to detect neural signals in the nerve. In other examples, the diagnostic implant 1 may detect one or more patient vital signs, for example body temperature, heart rate, electromyography (EMG), electrocardiogram (ECG), respiration rate, blood pressure, and/or blood gas concentration (e.g., oxygen, carbon dioxide, carbon monoxide). In this example, the position of the diagnostic implant 1 may be tested to ensure that the electrodes 4 are correctly positioned relative to the nerve 9 in order to detect neural signals.

In such examples the delivery system 10 for a diagnostic implant 1 may include a sensor 45 like that illustrated in FIG. 14. In the illustrated example the sensor 45 is attachable to the patient, in particular the patient's skin 5. The sensor 45 may be adhered to the skin 5, or otherwise held in place, for example by a strap or as a wearable. In other examples, the sensor 45 may be provided in the delivery device 10 itself, for example in the handle 11. In other examples, the sensor 45 may be provided in a wearable device that accompanies the neurostimulator implant, for example a wearable that provides wireless power and control after implantation is completed.

In examples, the sensor 45 may detect the same neural signal as the diagnostic implant 1 in order to test the diagnostic implant 1. For example, the sensor 45 may be arranged to detect one or more neural signals, including an action potential (nerve impulse), electrical impedance in the tissue, a nerve response (e.g., nerve response amplitude), electrical interference, motor neuron response (e.g., using electromyography (EMG)), electrodermal activity (EDA), and/or heart rate characteristics (e.g., using an electrocardiogram (ECG)). In other examples, the diagnostic implant may detect one or more patient vital signs, for example body temperature, heart rate, respiration rate, blood pressure, and/or blood gas concentration (e.g., oxygen, carbon dioxide, carbon monoxide).

As shown in FIG. 14, the delivery device 10 may also include a controller 46. The controller 46 may be embedded within the handle 11, or provided separately, for example in a separate device. The controller 46 is in communication with the sensor 45 and the power delivery system 37. Communication is provided by communication channel 44, which may be a wired connection or a wireless communications channel.

The controller 46 may be configured to control the power delivery system 37. For example, a user input may instruct the controller 46 to control the power delivery system 37 to power the medical implant 1. A user input may be provided through a button or switch on the delivery device 10, or through a graphical user interface, GUI, 43 as illustrated.

In examples, the controller 46 may be adapted to control the power delivery system 37 to power the medical implant 1 based on (i.e., in response to) the characteristic detected by sensor 45. In particular, the controller 46 may be configured to test the position of the medial implant 1 by powering the medical implant through the power delivery system 37 and using the data from the sensor 45 to assess the positioning of the medical implant 1. The controller 46 may be configured to increase or decrease the power provided to the medical implant 1 in response to the characteristic detected by the sensor 45. The controller 46 may additionally be in direct wireless communication with the medical implant 1 in order to control the medical implant 1 during testing.

As illustrated in FIG. 14, the delivery device 10 may further include a graphical user interface, GUI, 43. The GUI 43 may be mounted to the handle 11, or provided separately. The GUI 43 is in communication with the controller 46 and may be controlled by the controller 46. The controller 46 may display, on the GUI 43, one or more of the following:

- characteristics of the power provided to the medical implant (e.g., frequency, voltage, current);
- an operating characteristic of the medical implant (e.g., frequency, amplitude);
- one or more characteristics detected by the sensor 45; and/or
- one or more thresholds of the characteristics detected by the sensor 45.

In some examples, the controller 46 displays, on the GUI 43, an overlay or comparison of the operating characteristics of the medical implant 1 and the data received from the sensor 45. Such an overlay or comparison may illustrate an effectiveness of the positioning and operation of the medical implant 1.

In some examples, the delivery device 10 may include a user input device, such as a button or switch. In an example, the GUI 43 is a touchscreen device operable as the user input device. In response to a user input through the user input device the controller 46 may be configured to perform a test program, for example by powering the medical implant 1 and detecting a characteristic of the patient by the sensor 45.

In examples, the GUI 43 may include an input for patient/visual feedback. For example, the GUI 43 may include an input for the user to input a rating of the patient's pain or tingling sensation. In examples, the GUI 43 may include a user input for inputting information about feedback, e.g., to rate or confirm the effectiveness of the position of the medical implant 1. In other examples, the GUI 43 may include a user input for confirming that feedback has been observed.

FIGS. 15 to 18 illustrate further examples of the delivery device 10 in which the delivery device 10 includes an impedance sensor system 47 arranged to detect a change in tissue type at or near a tip of the delivery sheath by measuring an electrical impedance, as described below.

Figure 15:
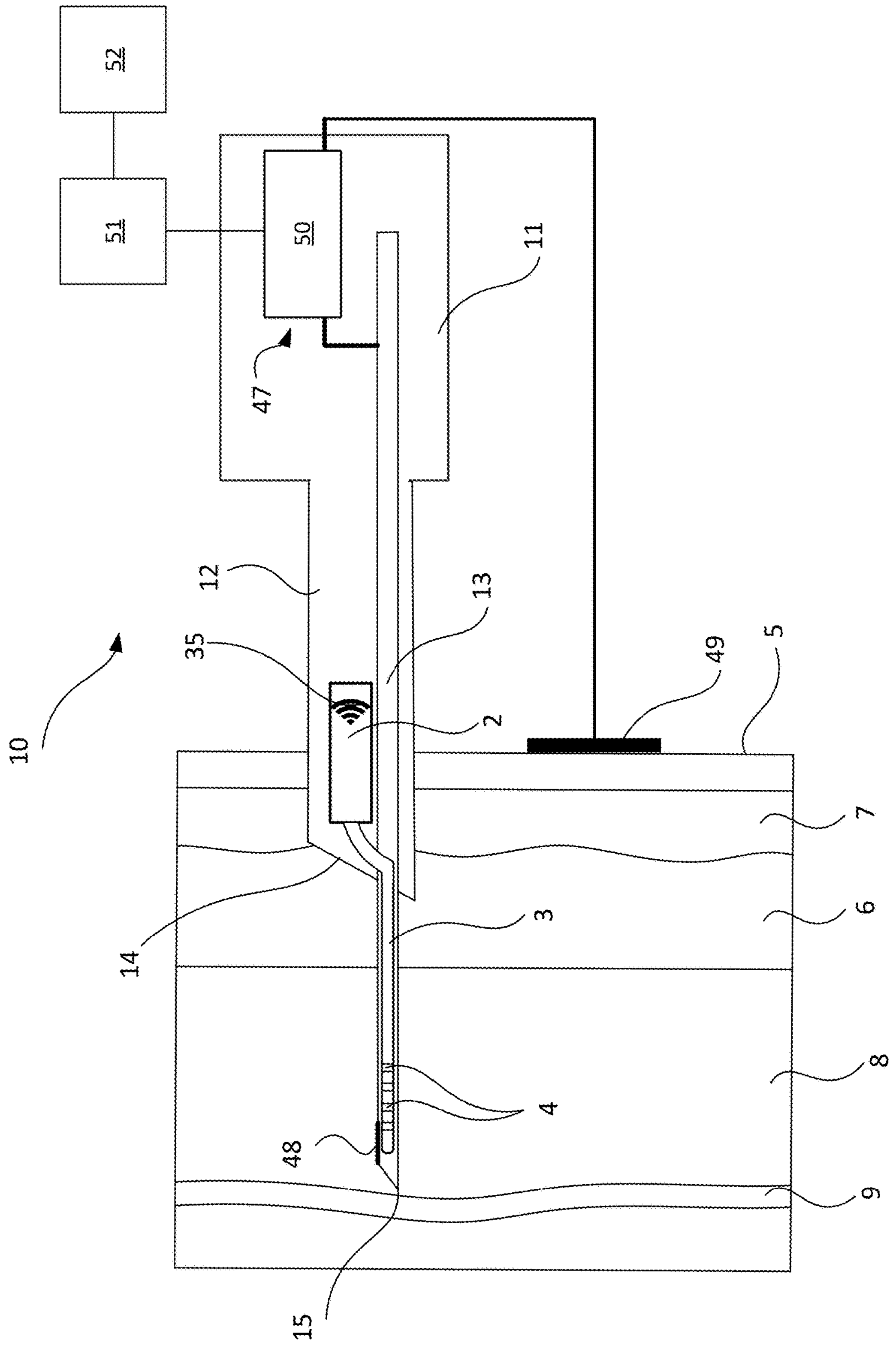
FIG. 15 illustrates an example delivery device having first and second needles and an impedance sensor system.

FIG. 15 illustrates an example based on the delivery device 10 described with reference to FIGS. 5A to 10, in which the delivery device 10 has a delivery sheath comprising a first needle 12 that holds the housing portion 2 of the medical implant 1, and a second needle 13 that holds the electrode lead 3. It will be appreciated that the impedance sensor system 47 described below may be used in combination with the power delivery system 37 described with reference to FIGS. 5A to 5D, or the power delivery system 37 may be omitted.

As shown in FIG. 15, the impedance sensor system 47 comprises a first electrode 48 positioned at or near the tip 15 of the second needle 13. The first electrode 48 is connected to an impedance analyser 50 located, in this example, in the handle 11. The first electrode 48 may be a separate component attached to the second needle 13, or the second needle 13 may comprise an electrically insulative coating with an opening that exposes a portion of the second needle 13 and defines the first electrode 48.

The impedance sensor system 47 also comprises a second electrode 49 that is arranged to contact the patient at a position spaced from the first electrode 48. In the illustrated example the second electrode 49 is positionable (e.g., adherable) against the patient's skin 5. However, the second electrode 49 may alternatively protrude from the handle 11, or the second electrode 49 may be provided on the first needle 12, or the second electrode 49 may be provided on the second needle 13, spaced and electrically insulated from the first electrode 48.

Both the first electrode 48 and the second electrode 49 are connected to an impedance analyser 50 that detects an electrical impedance across the first and second electrodes 48, 49. The electrical impedance may be indicative of the tissue type in the vicinity of the first electrode 48, i.e., at the tip 15 of the second needle 13. For example, the detected electrical impedance may have a first value when the first electrode 48 is within the subcutaneous tissue 6, a second value when the first electrode 48 is within the muscle 8, and a third value when the first electrode 48 is close to the nerve 9. Accordingly, the detected electrical impedance may be indicative of the position of the first electrode 48 (and the tip 15 of the second needle 13) in the patient's tissue.

Tissue boundaries are particularly pronounced when detecting electrical impedance and so changes in detected electrical impedance can be used to determine the position of the tip 15 of the second needle 13 relative to tissue boundaries. In examples, the detected electrical impedance may be used to determine when the tip 15 of the second needle 13 is approaching a nerve 9.

In examples, the detected electrical impedance may be used in conjunction with ultrasound to guide the second needle 13 to an appropriate implantation position. In particular, ultrasound can be used to guide the second needle 13 through the skin 5 and muscle 8, towards the nerve 9, and the detected electrical impedance can be used to determine when the tip 15 of the second needle 13 is an appropriate distance from the nerve 9. The detected electrical impedance may help to prevent puncture of the nerve 9 by the second needle 13.

As shown in FIG. 15, the impedance analyser 50 is in communication with a controller 51. The controller 51 may analyse the detected electrical impedance determined by the impedance analyser. The controller 51 and impedance analyser 50 may be a single component. The delivery device 10 may also include a graphical user interface, GUI, 52 in communication with the controller 51. The controller 51 may display, on the GUI 52, the detected electrical impedance. The controller 51 may also display, on the GUI 52, one or more thresholds of electrical impedance. The controller 51 may display, on the GUI 52, an historical track of the detected electrical impedance as the first electrode 48 has passed through the skin 5 and tissue of the patient. The controller 51 may compare the detected electrical impedance to a database or other comparable data, for example to determine a tissue type or anatomical feature based on the detected electrical impedance and specifically a change in the detected electrical impedance. The database or comparable data may be provided in a distributed location (e.g., on a server) and the impedance analyser may communicate via a wireless communications channel (e.g., via the internet).

Figure 16:
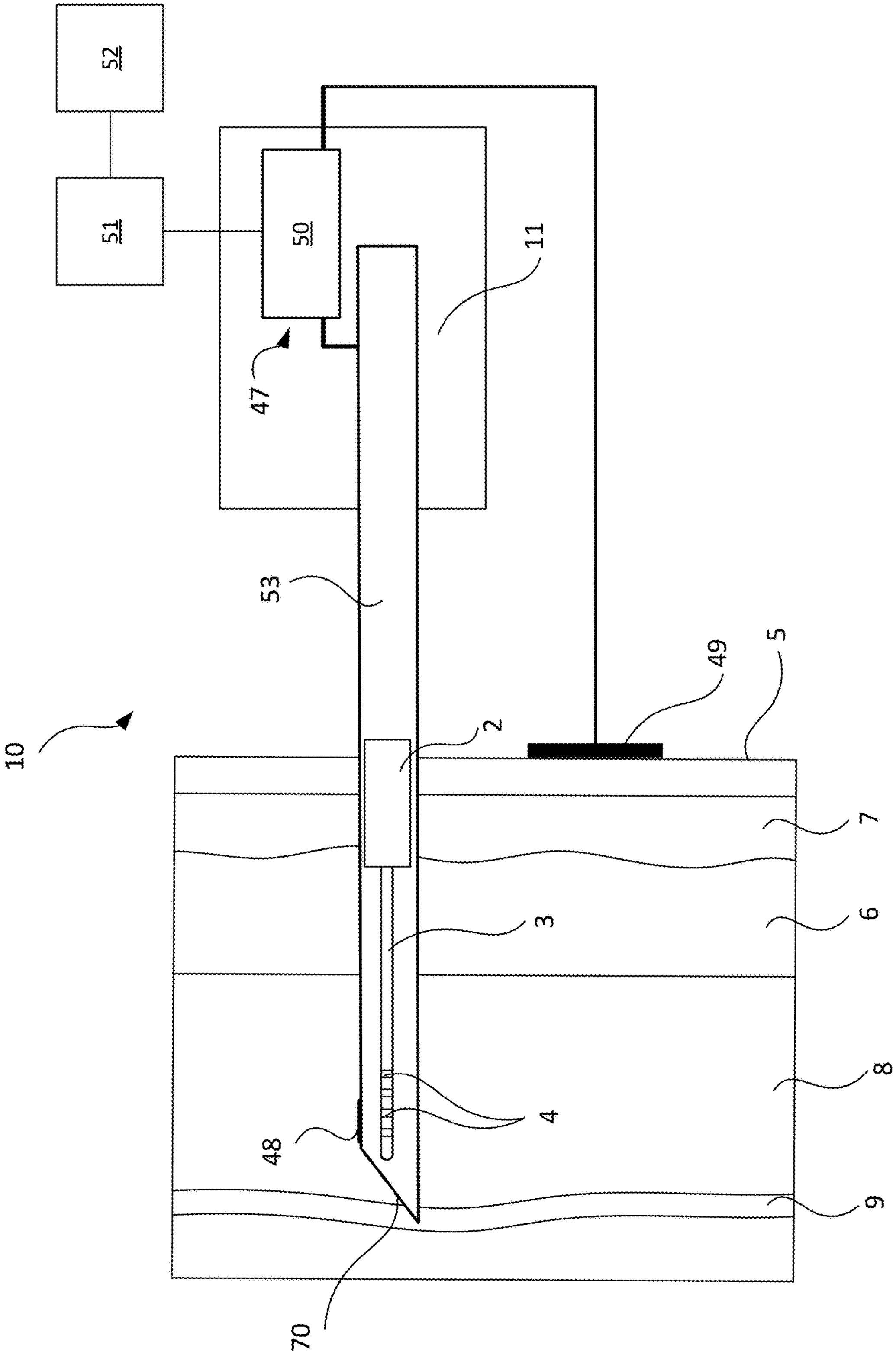
FIG. 16 illustrates an example delivery device having a cannula and an impedance sensor system.

FIG. 16 illustrates a further example delivery system 10 with an impedance sensor system 47. This example is based on the delivery device 10 described with reference to FIGS. 11A to 11D, in which the delivery device 10 has a delivery sheath comprising a cannula 53 that holds the medical implant 1. It will be appreciated that the impedance sensor system 47 described below may be used in combination with the power delivery system 37 described with reference to FIGS. 11A to 11D, or the power delivery system 37 may be omitted.

As shown in FIG. 16, the cannula 53 comprises the first electrode 48 formed at or near a tip 70 of the cannula 53. The first electrode 48 may be a separate component attached to the cannula 53, or the cannula 53 may comprise an electrically insulative coating with an opening that exposes a portion of the cannula 53 and defines the first electrode 48.

The impedance sensor system 47 also comprises a second electrode 49 that is arranged to contact the patient at a position spaced from the first electrode 48. In the illustrated example the second electrode 49 is positionable (e.g., adherable) against the patient's skin 5. However, the second electrode 49 may alternatively protrude from the handle 11, or the second electrode 49 may be provided on the cannula 53, spaced and electrically insulated from the first electrode 48.

The impedance sensor system 47 of FIG. 16 works in the same manner as described above with reference to FIG. 15.

In some examples, the cannula 53 illustrated in FIG. 16 may be a needle with a bevel tip.

Figure 17:
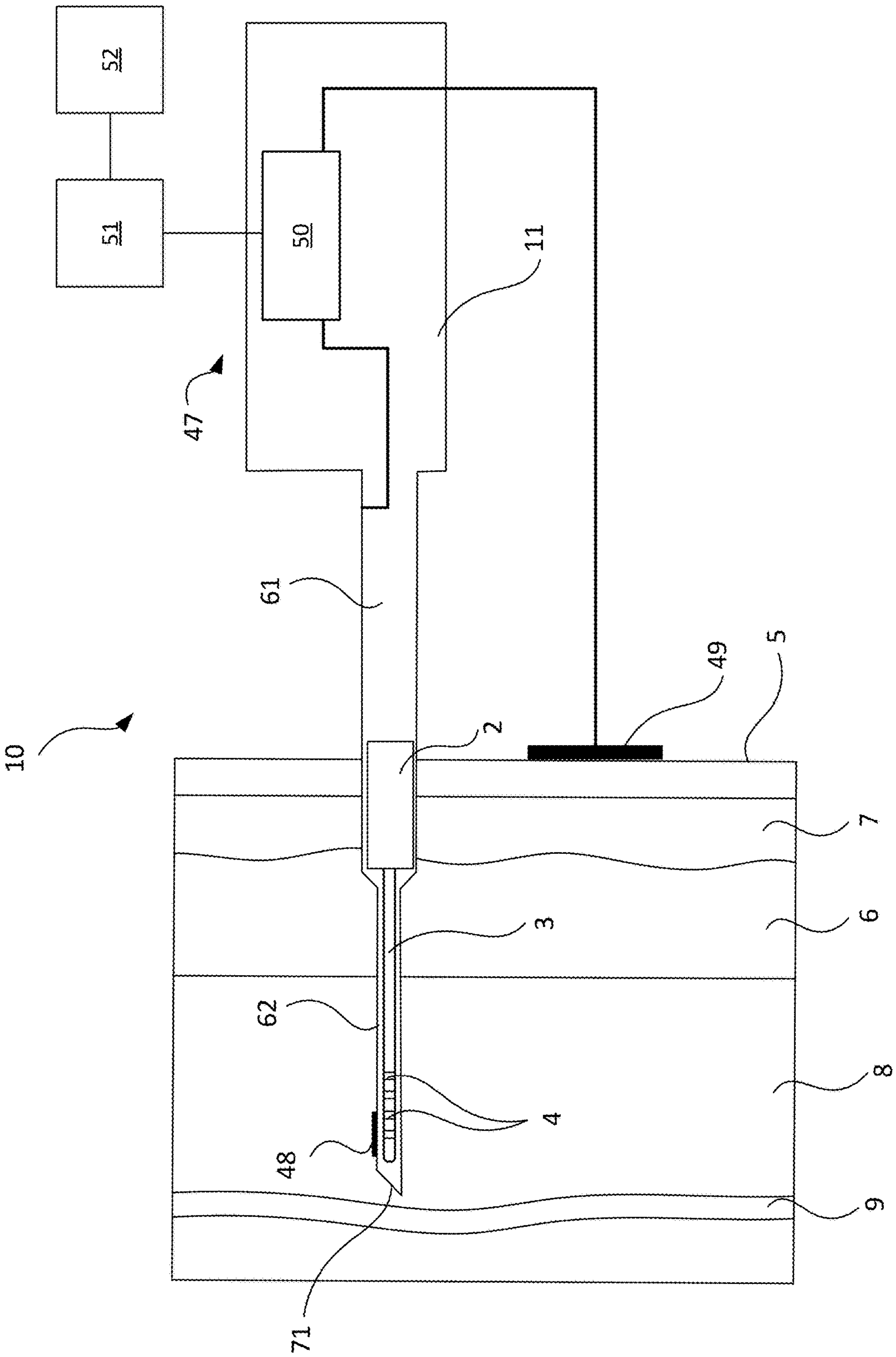
FIG. 17 illustrates an example delivery device having a delivery sheath with first and second portions, and an impedance sensor system.

FIG. 17 illustrates a further example delivery system 10 with an impedance sensor system 47. This example is based on the delivery device 10 described with reference to FIGS. 12A to 12C, in which the delivery device 10 has a delivery sheath comprising a first portion 61 and a second portion 62 fixed to each other and holding the housing portion 2 and electrode lead 3 of the medical implant 1, respectively. The first portion 61 has a greater diameter than the second portion 62. It will be appreciated that the impedance sensor system 47 described below may be used in combination with the power delivery system 37 described with reference to FIGS. 12A to 12C, or the power delivery system 37 may be omitted.

As shown in FIG. 17, the second portion 62 comprises the first electrode 48 formed at or near a tip 71 of the second portion 62. The first electrode 48 may be a separate component attached to the second portion 62, or the second portion 62 may comprise an electrically insulative coating with an opening that exposes a portion of the second portion 62 and defines the first electrode 48.

The impedance sensor system 47 also comprises a second electrode 49 that is arranged to contact the patient at a position spaced from the first electrode 48. In the illustrated example the second electrode 49 is positionable (e.g., adherable) against the patient's skin 5. However, the second electrode 49 may alternatively protrude from the handle 11, or the second electrode 49 may be provided on the first portion 61 or on the second portion 62, spaced and electrically insulated from the first electrode 48.

The impedance sensor system 47 of FIG. 76 works in the same manner as described above with reference to FIG. 15.

Figure 18:
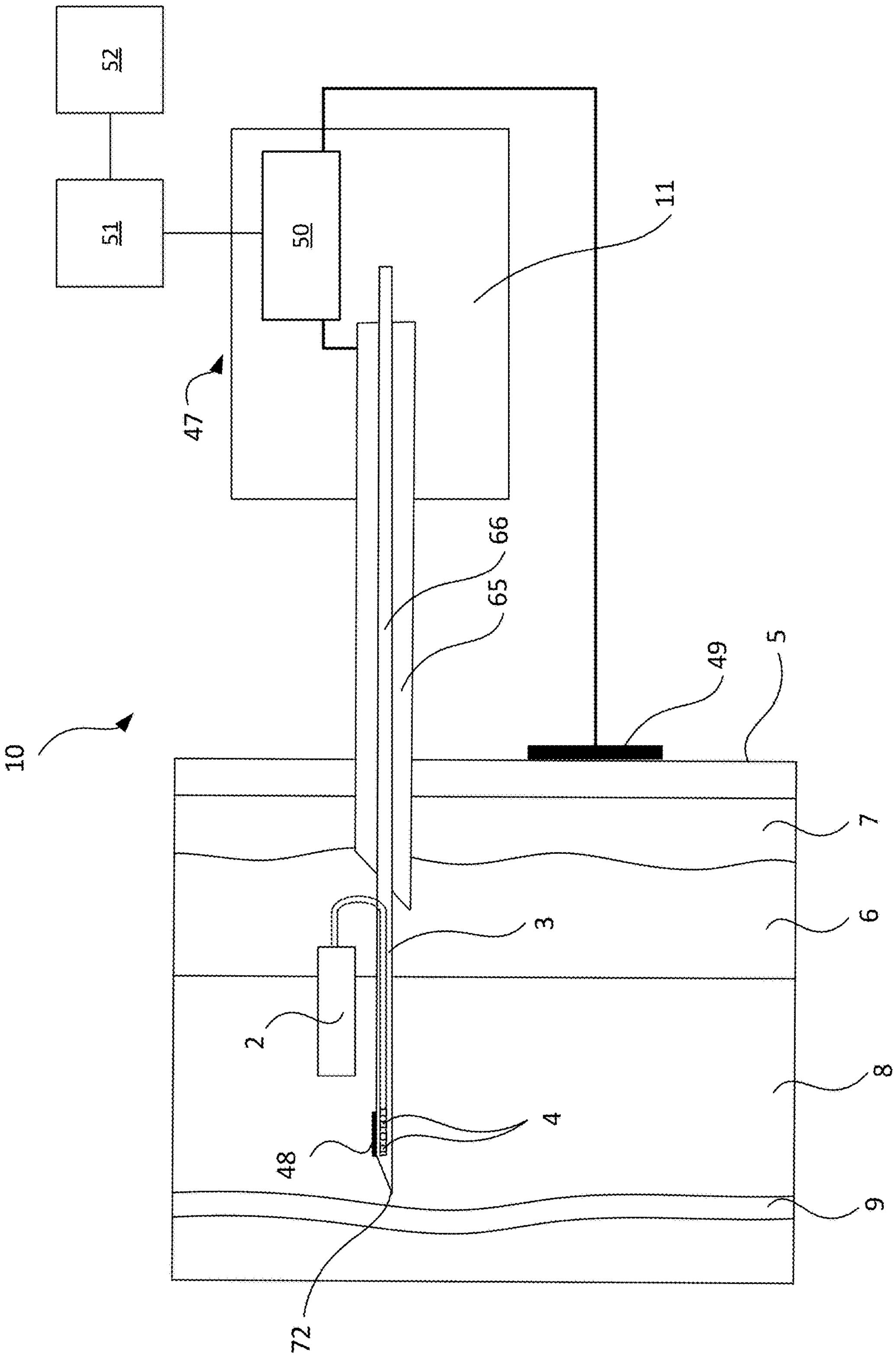
FIG. 18 illustrates an example delivery device operable to deliver the medical implant in a reverse orientation, and having an impedance sensor system.

FIG. 18 illustrates a further example delivery system 10 with an impedance sensor system 47. This example is based on the delivery device 10 described with reference to FIGS. 13A and 13B, in which the delivery device 10 has a delivery sheath comprising a first needle 65 and a second needle 66 arranged to deliver the medical implant 1 in a reverse orientation. It will be appreciated that the impedance sensor system 47 described below may be used in combination with the power delivery system 37 described with reference to FIGS. 13A and 13B, or the power delivery system 37 may be omitted.

As shown in FIG. 18, the second needle 66 comprises the first electrode 48 formed at or near a tip 72 of the second needle 66. The first electrode 48 may be a separate component attached to the second needle 66, or the second needle 66 may comprise an electrically insulative coating with an opening that exposes a portion of the second needle 66 and defines the first electrode 48.

The impedance sensor system 47 also comprises a second electrode 49 that is arranged to contact the patient at a position spaced from the first electrode 48. In the illustrated example the second electrode 49 is positionable (e.g., adherable) against the patient's skin 5. However, the second electrode 49 may alternatively protrude from the handle 11, or the second electrode 49 may be provided on the first needle 65 or on the second needle 66, spaced and electrically insulated from the first electrode 48.

The impedance sensor system 47 of FIG. 18 works in the same manner as described above with reference to FIG. 15.

Figure 19:
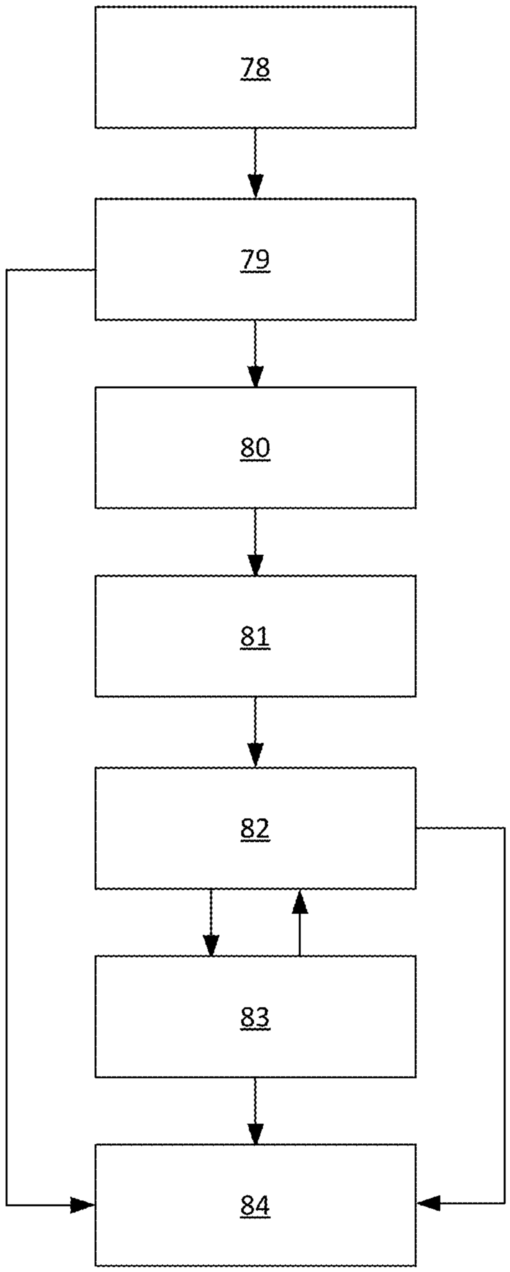
FIG. 19 schematically illustrates a method of implanting a medical implant.

FIG. 19 schematically illustrates operation of the various delivery devices 10 to implant a medical implant 1. The illustrated method may be used with any of the medical implants 1 described herein, and with any of the delivery devices 10 described herein. The method uses a delivery device 10 holding the medical implant 1 as previously described.

As shown in FIG. 19, the method comprises percutaneously positioning the delivery sheath of the delivery device in a patient's tissue 78. The delivery sheath is passed through the skin and into the underlying tissue of the patient. An ultrasound scanner may be used to visualise the position of the delivery sheath, allowing the operator to guide the delivery sheath towards the nerve.

The method further comprises detecting an electrical impedance between a tip of the delivery sheath and another location on the patient 79. The electrical impedance can be detected using the impedance sensor system 47 described with reference to FIGS. 15 to 18. As described above, the detected electrical impedance may be indicative of the proximity of the delivery sheath to the nerve tissue boundary, and so the detected electrical impedance may be used by the operator to ensure close proximity of the delivery sheath to the nerve, without damaging the nerve.

In some examples the above method may be used to position the delivery sheath appropriately relative to the nerve to implant the medical implant. In such examples, the method may comprise releasing the medical implant from the delivery device and withdrawing the delivery sheath from the patient 84.

Optionally, the method may include partially exposing electrodes of the medical implant 80. In various examples as described above, this may comprise retracting a part of the delivery sheath, or pushing the medical implant partially out of the delivery sheath.

The method may further comprise powering the medical implant within the delivery device 81. In particular, as described in detail above, a power delivery system of the delivery device may be operated to power the medical implant within the delivery device.

The method may further comprise assessing a position of the electrodes 82. In particular, if the medical implant comprises a neurostimulator implant, the method may further comprise detecting a reaction of the patient to assess the position of the electrodes. Alternatively, if the medical implant is a diagnostic implant the method may comprise testing the diagnostic reading 82 to assess the position of the electrodes.

Based on the assessed position of the electrodes, the method may comprise repositioning the delivery sheath and electrodes 83. Once the electrodes have been repositioned the position of the electrodes may be assessed again 82, and so on until the position of the electrodes is acceptable.

Finally, the method may comprise deploying the medical implant and withdrawing the delivery sheath from the patient 84.

At various places in the present specification, values are disclosed in groups or in ranges. It is specifically intended that the description include each and every individual subcombination of the members of such groups and ranges and any combination of the various endpoints of such groups or ranges. For example, an integer in the range of 0 to is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Similarly, for example, a real number in the range of 0.00 to 40.00 is specifically intended to individually disclose all real numbers between 0.00 and 40.00.

Throughout the description and claims of this specification, the words "comprise" and "contain" and variations of them mean "including but not limited to", and they are not intended to (and do not) exclude other components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

What is claimed is:

1. A delivery device for percutaneously implanting a neurostimulator implant in tissue of a patient, the neurostimulator implant comprising a housing portion, an elongate electrode lead extending from the housing portion, and a wireless power receiver, the delivery device comprising:

a delivery sheath adapted to at least partially surround the neurostimulator implant and carry the neurostimulator implant for percutaneous delivery in the patient's tissue, the delivery sheath comprising a first portion adapted to hold the housing portion of the neurostimulator implant, and a second portion protruding from the first portion and adapted to hold the elongate electrode lead of the neurostimulator implant, the second portion having a smaller diameter than the first portion and being retractable relative to the first portion, and a power delivery system comprising a wireless power transmitter adapted to transmit wireless power to the wireless power receiver of the neurostimulator implant to provide electric power to the neurostimulator implant within the delivery sheath.

2. The delivery device of claim 1, wherein the wireless power transmitter is disposed in the delivery sheath.

3. The delivery device of claim 1, further comprising a power source.

4. The delivery device of claim 1, wherein the delivery device comprises a handle and the delivery sheath extends from the handle.

5. The delivery device of claim 1, wherein the delivery sheath comprises a needle, or a cannula.

6. The delivery device of claim 1, wherein the delivery device further comprises a sensor operable to detect a reaction of the patient when the power delivery system provides electric power to the neurostimulator implant during percutaneous delivery.

7. The delivery device of claim 6, wherein the sensor is configured to detect a movement reaction of the patient.

8. The delivery device of claim 6, wherein the sensor is configured to detect neural signals.

9. The delivery device of claim 6, further comprising a graphical user interface operable to display information received from the sensor.

10. The method of claim 1, comprising testing the position of the neurostimulator implant by powering the neurostimulator implant within the delivery sheath by the power delivery system of the delivery device.

11. The method of claim 10, comprising retracting the second portion of the delivery sheath to expose an electrode of the neurostimulator implant while testing the position of the medical implant.

12. The method of claim 11, comprising repositioning the delivery sheath based on feedback from testing the position of the neurostimulator implant.

13. The method of claim 1, wherein the neurostimulator implant is a battery-less implant, and wherein the power delivery system is configured to provide power for operation of the neurostimulator implant when the neurostimulator implant is received in the delivery sheath.

14. The delivery device of claim 1 in combination with a neurostimulator implant comprising a housing portion and an elongate electrode lead extending from the housing portion, and the neurostimulator implant being battery-less and comprising a wireless power receiver, and wherein the housing portion of the neurostimulator implant is receivable in the first portion of the delivery sheath and the elongate electrode lead of the neurostimulator implant is receivable in the second portion of the delivery sheath.

15. A delivery device for percutaneously implanting a neurostimulator implant in tissue of a patient, the neurostimulator implant comprising a housing portion, an elongate electrode lead extending from the housing portion, and a wireless power receiver, the delivery device comprising:

a delivery sheath adapted to at least partially surround the neurostimulator implant and carry the neurostimulator implant for percutaneous delivery in the patient's tissue, the delivery sheath comprising a first needle adapted to hold the housing portion of the neurostimulator implant, and a second needle protruding from the first needle and adapted to hold the elongate electrode lead of the neurostimulator implant, the second needle having a smaller diameter than the first needle and being retractable relative to the first needle, and an impedance sensor comprising a first electrode at or near a tip of the second needle and a second electrode arranged to contact the patient at a location spaced from the first electrode, wherein the impedance sensor is operable to detect an electrical impedance between the first electrode and the second electrode to detect a change in the tissue at the tip of the first needle of the delivery sheath during percutaneous delivery of the neurostimulator implant so as to detect when the tip of the first needle approaches or passes a nerve-tissue boundary.

16. The delivery device of claim 15, wherein the second electrode is positionable against the skin of the patient proximate to the percutaneous delivery site.

17. The delivery device of claim 15, further comprising an impedance analyser configured to analyse the detected electrical impedance.

18. The delivery device of claim 17, wherein the impedance analyser is configured to compare the detected electrical impedance to a threshold value.

19. The delivery device of claim 17, further comprising a graphical user interface to display information received from the impedance analyser.

20. The delivery device of claim 15, further comprising a power delivery system adapted to provide electrical power to the medical implant within the delivery sheath.

* * * * *